United States Patent
Lomas et al.

(10) Patent No.: US 11,234,086 B2
(45) Date of Patent: Jan. 25, 2022

(54) ACOUSTIC DEVICES

(71) Applicant: HEMIDEINA PTY LTD, Victoria (AU)

(72) Inventors: Kathryn Lomas, Victoria (AU); Andrew Reid, Victoria (AU); Toby McSweeney, Victoria (AU); Daniel Trott, Victoria (AU); James Windmill, Victoria (AU); Joseph Jackson, Victoria (AU)

(73) Assignee: HEMIDEINA PTY LTD, Victoria (AU)

( * ) Notice: Subject to any disclaimer, the term of this patent is extended or adjusted under 35 U.S.C. 154(b) by 0 days.

(21) Appl. No.: 17/282,115

(22) PCT Filed: Jan. 10, 2020

(86) PCT No.: PCT/AU2020/050013
§ 371 (c)(1),
(2) Date: Apr. 1, 2021

(87) PCT Pub. No.: WO2020/142812
PCT Pub. Date: Jul. 16, 2020

(65) Prior Publication Data
US 2021/0321207 A1    Oct. 14, 2021

(30) Foreign Application Priority Data

Jan. 11, 2019  (AU) .................................. 2019900079
Jul. 29, 2019  (AU) .................................. 2019902691

(51) Int. Cl.
*H04R 25/00*  (2006.01)
*A61N 1/05*   (2006.01)
(Continued)

(52) U.S. Cl.
CPC ......... *H04R 25/606* (2013.01); *A61N 1/0541* (2013.01); *H01L 41/183* (2013.01);
(Continued)

(58) Field of Classification Search
CPC ................ H04R 25/606; H04R 25/609; H04R 417/025; H04R 17/10; H04R 25/658;
(Continued)

(56) References Cited

U.S. PATENT DOCUMENTS

| | | |
|---|---|---|
| 6,782,112 B1 | 8/2004 | Geddes |
| 2009/0140612 A1 | 6/2009 | Ikeuchi |
| 2017/0006385 A1 | 1/2017 | Kim |

FOREIGN PATENT DOCUMENTS

| | | | |
|---|---|---|---|
| WO | WO-2010/119259 A1 | 10/2010 | |
| WO | WO-2012/153911 A1 | 11/2012 | |
| WO | WO-2020142812 A1 * | 7/2020 | ........... H04R 25/606 |

OTHER PUBLICATIONS

Hyejin Jeon et al., "Characterization of a Piezoelectric AlN beam Array in Air and Fluid for an Artificial Basilar Membrane", Electronic Materials Letters (2018), Feb. 19, 2018, pp. 101-110.

\* cited by examiner

*Primary Examiner* — Phylesha Dabney
(74) *Attorney, Agent, or Firm* — Blank Rome LLP

(57) ABSTRACT

An acoustic device, comprising: a device body comprising: an acoustic membrane having a first surface and a second surface opposite the first surface; and at least one acoustic cavity formed adjacent the first surface of the acoustic membrane; a plurality of piezoelectric beam resonators supported over the first surface of the acoustic membrane and separated from the first surface by the at least one acoustic cavity, each of the plurality of piezoelectric beam resonators having at least one different natural frequency; wherein each of the plurality of piezoelectric beam resona- (Continued)

tors is configured to oscillate in response to sound pressure waves incident at the acoustic device.

48 Claims, 17 Drawing Sheets

(51) Int. Cl.
*H01L 41/18* (2006.01)
*H04R 17/02* (2006.01)
*H04R 17/10* (2006.01)

(52) U.S. Cl.
CPC ........... *H04R 17/025* (2013.01); *H04R 17/10* (2013.01); *H04R 25/554* (2013.01); *H04R 25/609* (2019.05); *H04R 25/658* (2013.01); *H04R 2225/023* (2013.01); *H04R 2225/025* (2013.01); *H04R 2225/57* (2019.05); *H04R 2225/67* (2013.01); *H04R 2225/77* (2013.01)

(58) Field of Classification Search
CPC .......... H04R 2225/57; H04R 2225/023; H04R 2225/025; H04R 2225/67; H04R 2225/77; H01L 41/183
See application file for complete search history.

ACOUSTIC DEVICES

CROSS-REFERENCE TO RELATED APPLICATIONS

This application is based on PCT/AU2020/050013, filed Jan. 10, 2020, which claims priority to Australian patent application No. 2019900079, filed Jan. 11, 2019 and Australian patent application No. 2019902691, filed Jul. 29, 2019, the entirety of each of which is incorporated by reference herein.

TECHNICAL FIELD

The present disclosure relates to acoustic devices, such as transducers, acoustic sensors, and microphones, in particular, in-ear acoustic devices for cochlear implants and other implantable hearing devices.

BACKGROUND

A cochlear implant is a surgically implanted neuroprosthetic device that provides a sense of sound to a person with severe to profound sensorineural hearing loss. Current cochlear, bone conduction and hearing implants have both implanted components and external components. Visible external components typically include microphones, sound processing electronics and a battery, which provide a visible indication of the user's disability. Miniaturisation of these external components is challenging due to the requirement for a large power source to drive the sound processing electronics.

It is desired to address or ameliorate one or more shortcomings of conventional cochlear implant technology, or to at least provide a useful alternative thereto.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

SUMMARY

According to an aspect of the disclosure, there is provided an acoustic device, comprising: a device body comprising: an acoustic membrane having a first surface and a second surface opposite the first surface; and at least one acoustic cavity formed adjacent the first surface of the acoustic membrane; a plurality of piezoelectric beam resonators supported over the first surface of the acoustic membrane and separated from the first surface by the cavity, each of the plurality of piezoelectric beam resonators having at least one different natural frequency; wherein each of the plurality of piezoelectric beam resonators is configured to oscillate in response to sound pressure waves incident at the acoustic device.

The acoustic membrane may be configured to oscillate in response to sound pressure waves incident on the second surface of the acoustic membrane. In some embodiments, the oscillation of the acoustic membrane may cause the plurality of piezoelectric beam resonators to oscillate. In any case, the acoustic membrane may act as a baffle, increasing the sound shadow on the first and second surfaces of the device, thereby amplifying the sound around the piezoelectric beam resonators and increasing the displacement in response to incident sound waves.

Each of the piezoelectric beam resonators may differ in one or more of beam length, beam width, beam thickness, beam composition, and beam compliance.

The piezoelectric beam resonators may be planar. The piezoelectric beam resonators may be configured to be parallel to each other and the first surface of the acoustic membrane.

The at least one cavity may comprise a respective cavity for each of the plurality of piezoelectric beam resonators. Alternatively, the at least one cavity may comprise a single cavity. For example, the plurality of piezoelectric beam resonators may share the single cavity.

The plurality of piezoelectric beam resonators may comprise four or more piezoelectric beam resonators. The plurality of piezoelectric beam resonators may have successively decreasing beam lengths, such that their fundamental resonant frequencies correspond to different frequency channels.

In some embodiments, for example where the acoustic device is incorporated into an apparatus configured to be positioned in an ear canal, the acoustic membrane may be circular or oval in shape so as to conform with the shape of the ear canal. In other embodiments, the acoustic device may be square or rectangular in shape.

The piezoelectric beam resonators may be double-clamped piezoelectric beam resonators or cantilever resonators.

A plurality of electrodes may be provided on the device body and electrically coupled to the plurality of piezoelectric beam resonators for transferring electrical signals away from the acoustic device to, for example, sensing electronics. The electrodes may be formed with the piezoelectric beam resonators, cavity and diaphragm by additive manufacturing. The electrodes may be formed from an electrically conductive nanostructure-polymer composite material.

In some embodiments, one or more of the piezoelectric beam resonators comprise a piezoelectric layer. The piezoelectric layer may extend along a portion of the length of its respective beam resonator adjacent the at least one acoustic cavity. For example, each respective piezoelectric layers may extends along between 10% and 20% of the length of its respective beam resonator adjacent the at least one acoustic cavity.

The piezoelectric beam resonators may be formed from a piezoelectric nanoparticle-polymer composite material. The acoustic membrane may be formed from a polymer material or a metallic material.

According to an aspect of the disclosure, there is provided an in-ear microphone, comprising: a first acoustic device as described above.

The in-ear microphone may further comprise a second acoustic device as described above. Each of the plurality of piezoelectric beam resonators of the first and second acoustic devices may have at least one different natural frequency. The first and second acoustic devices may be configured to transduce acoustic sound pressure waves at low and high frequency bands respectively.

The in-ear microphone may have an oval cross section so as to conform to the shape of an ear canal, whilst maximising the internal volume of the in-ear microphone to accommodate elements of the in-ear microphone.

The in-ear microphone may further comprise: an earbud enclosure having a first end, a second end, the earbud enclosure for insertion into a human ear canal by the first end.

In one embodiment, the first acoustic device may be located within the earbud enclosure such that the first surface of the first acoustic device faces an axis extending between the first end and the second end of the earbud enclosure. The in-ear microphone may further comprise a back cavity within the earbud enclosure adjacent the first acoustic device. The in-ear microphone may further comprise a first front cavity provided within the earbud enclosure adjacent the second surface of the first acoustic device. The second acoustic device may also be located within the earbud enclosure such that the first surface of the second acoustic device faces the axis extending between the first end and the second end of the earbud enclosure. The first surface may be adjacent the back cavity. The in-ear microphone may further comprise a second front cavity within the earbud enclosure adjacent the second surface of the second acoustic device. The in-ear microphone may further comprise a first acoustic port formed in the second end of the in-ear microphone and in communication with the first front cavity and a second acoustic port formed in the second end of the in-ear microphone and in communication with the second front cavity.

In another embodiment, the in-ear microphone may further comprise a first front cavity within the earbud enclosure adjacent the first surface of the first acoustic device. A first acoustic port may be formed in the second end of the in-ear microphone and in communication with the first front cavity. A rear acoustic port may be formed towards the first end of the in-ear microphone and in communication with the first front cavity. Where a second acoustic device is provided, a second front cavity may be formed within the earbud enclosure adjacent the first surface of the second acoustic device. A second acoustic port may then be formed in the second end of the in-ear microphone and in communication with the second front cavity. The second surfaces of the first and second acoustic devices may face an axis extending between the first and second ends of the earbud enclosure. Preferably, the rear acoustic port is in communication with the second front cavity.

One or more of the back cavity, the first front cavity, and second front cavity or any other portion of the earbud enclosure may be filled with an acoustic transmission medium, such as air, water, oil or other lipid.

The first surface of each of the first and second acoustic devices may be positioned substantially opposite one another. Alternatively the second surfaces of each of the first and second acoustic devices may be positioned substantially opposite one another.

The in-ear microphone may further comprise sensing electronics located within the earbud enclosure and electrically coupled to the plurality of piezoelectric beam resonators. The sensing electronics may be configured to process electrical signals from each of the plurality of piezoelectric beam resonators.

The sensing electronics may comprise one or more variable gain amplifiers and/or operation amplifiers.

The in-ear microphone may further comprise a transmitter configured to wired or wirelessly transmit one or more processed signals generated by the sensing electronics. The transmitter may be located within the earbud enclosure. In some embodiments, the transmitter may be a wireless transmitter comprising an inductive coil. The inductive coil may be located within the earbud enclosure at the first end. In some embodiments, the transmitter may be a Bluetooth (RTM) transmitter. In any case, the transmitter may be configured to transmit the one or more processed signals to an implantable hearing device, such as a cochlear implant, a bone anchored implant, or an implantable hearing aid.

The in-ear microphone may further comprise a power source.

The first and second acoustic devices may be configured to transduce acoustic sound pressure waves at low and high frequency bands respectively.

The earbud enclosure may be formed with the first and second acoustic devices by additive manufacturing.

The earbud enclosure may be formed from a biocompatible polymer material.

According to an aspect of the disclosure, there is provided an implantable hearing devices, such as a cochlear implant, comprising an acoustic device as described in any of the aspects above, or an in-ear microphone as described above.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

BRIEF DESCRIPTION OF DRAWINGS

Embodiments of the disclosure will now be described by way of example only with reference to the accompanying drawings, in which.

DESCRIPTION OF EMBODIMENTS

Embodiments of the present disclosure aim to overcome or at least alleviate difficulties associated with large non-implanted components of hearing systems, such as state of the art cochlear hearing systems.

Specifically, embodiments of the present disclosure relate to acoustic devices capable of transducing acoustic sound pressure waves into electrical signals with a reduced requirement for complex sound processing.

Figure 1:
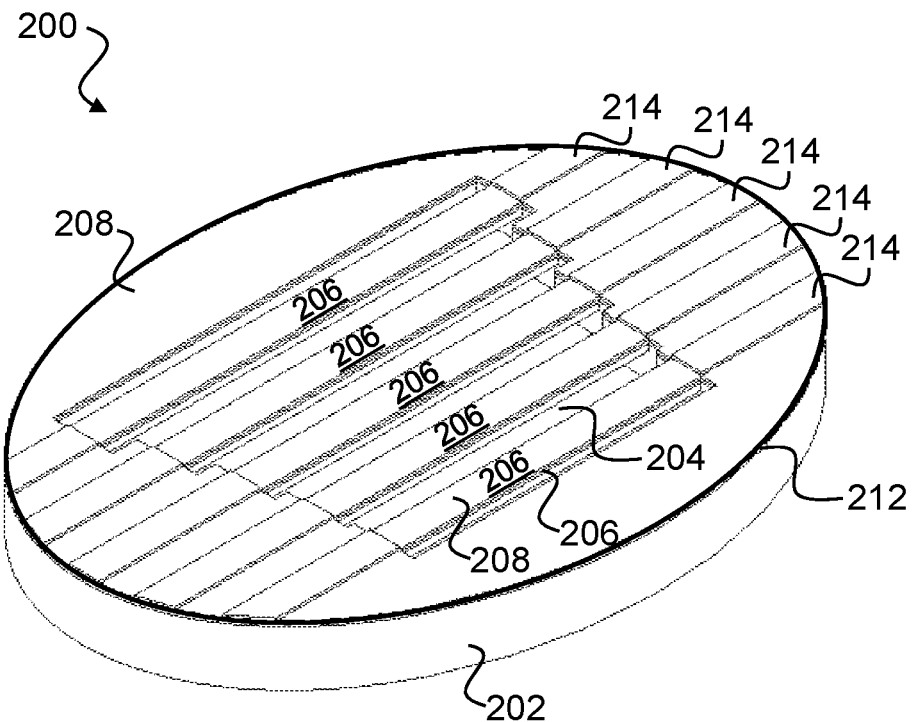
FIG. 1 is a diagram of an acoustic device according to embodiments of the present disclosure.
Figure 2:
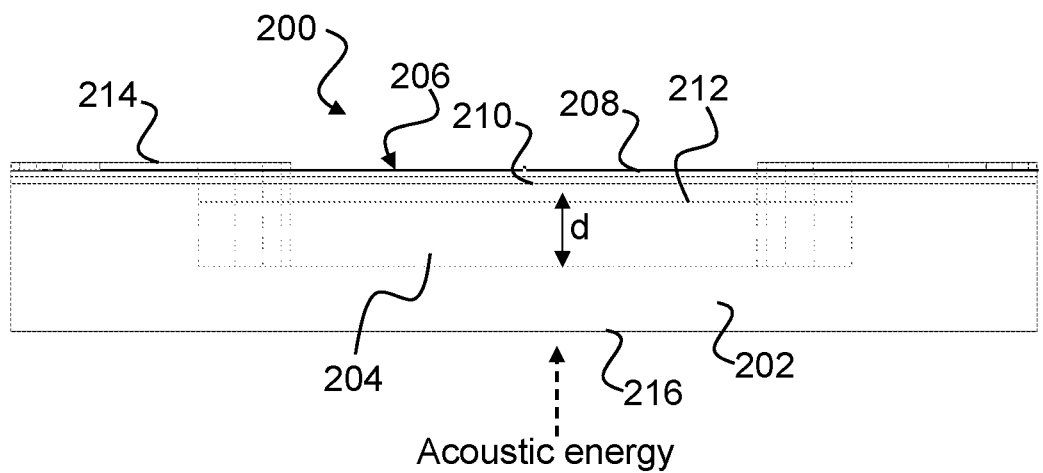
FIG. 2 is a side view of the acoustic device of FIG. 1.

FIGS. 1 and 2 are perspective and side views of an acoustic device 200 according to an embodiment of the present disclosure. The device 200 comprises an acoustic membrane 202 having a resonator cavity 204 formed therein. An array of clamped-clamped (double clamped) piezoelectric beam resonators 206 are supported over the resonator cavity 204. In some embodiments, the resonator cavity 204 has a depth, d, of between 200 and 500 microns. The effect of providing a relatively large gap between the acoustic membrane 202 and the beam resonators 206 is that it allows for greater displacement of the beam resonators 206, particularly in response to movement of the acoustic membrane 202. In the embodiment shown, a planar parallel array of beam resonators 206 are provided (individually referred to in FIG. 1 by reference numerals 206a, 206b, 206c, 206d and 206e). In other embodiments, the beam resonators 206 may be arranged in a non-planar and/or non-parallel fashion without departing from the scope of the present disclosure. In the embodiments described above, the beam resonators 206 are double-clamped. In other embodiments, the double-clamped resonators 206 may be replaced with cantilever beams, described in more detail below with reference to FIGS. 6 and 9, fixed at one end only without departing from the scope of the present disclosure.

Each of the piezoelectric beam resonators 206 may comprise a piezoelectric layer 208 and a ground layer 210 disposed beneath the piezoelectric layer 2018. One or both of the piezoelectric layer 208 and the ground layer 210 may extend across the entire surface of the device 200. Optionally, a resonator base 212 may be provided beneath the ground layer 210 of each beam resonator 206 to provide support and structure to each resonator 206. Electrodes 214 may be provided over the piezoelectric layer 208 to electrically couple each beam resonator 206 to external sensing electronics (not shown). Preferably, the electrodes 214 are positioned so as not to overlap the resonator cavity 204 or the beam resonators 206. Rather, the electrodes may be positioned at the sides of the device 200. Such sensing electronics may include variable gain amplifiers or operational amplifiers, such as hybrid junction field effect transistor (JFET) operational amplifiers or the like. Sensing circuits may be provided on an application specific integrated circuit (ASIC) or the like which may be coupled to the diaphragm or provided separately. Signal transmission electronics may also be provided with the sensing circuits as will be discussed in more detail below.

The piezoelectric beam resonators 206, cavity 204, diaphragm 202 and electrodes 214 may be formed by additive manufacturing (or three-dimensional (3D) printing). The additive manufacturing may, for example, comprise projection micro stereolithography (or stereo-lithographic printing (SLP) or digital light processing (DLP)). Suitable projection micro stereolithography techniques and materials are described in 3D *Optical Printing of Piezoelectric Nanoparticle-Polymer Composite Materials*, ACS Nano 8(10), July 2014. The piezoelectric beam resonators 206, cavity 204, diaphragm 202 and electrodes 214 may alternatively be formed using printed circuit board (PCB) manufacturing processes. Such processes may comprise one or more of photosensitive etching, copper-alloy plating, etc. as is known in the art.

The diaphragm 202 may be formed from a polymer material, for example, polyethylene glycol diacrylate (PEGDA). The electrodes 214 may be formed from an electrically conductive nanostructure-polymer composite material, for example, a carbon nanotube (CNT)-PEGDA composite material. The piezoelectric layer 208 of the piezoelectric beam resonators 206 may be formed from a piezoelectric nanoparticle-polymer composite material, for example, a barium titanate ($BaTiO_3$, BTO)-PEGDA composite material. Other equivalent conductive and piezoelectric polymer composite materials may also be used.

During operation, the acoustic device 200 is configured such that a cavity or void (not shown) is provided adjacent an external wall 216 of the membrane 202, the membrane configured to receive incident sound pressure waves at the external wall 216 of the membrane 202 which cause the membrane 202 to oscillate. Movement of the membrane 202 in turn induces motion in the array of beam resonators 206 which causes changes in capacitive strain in each of the beam resonators 206. Piezoelectrically transduced signals are then captured by the electrodes 214. By providing a cavity adjacent the external wall 216 of the membrane 202 which allows the membrane 202 to oscillate, the inventors have realised that the amount of sound energy captured by the acoustic device 200 is substantially increased.

Figure 3:
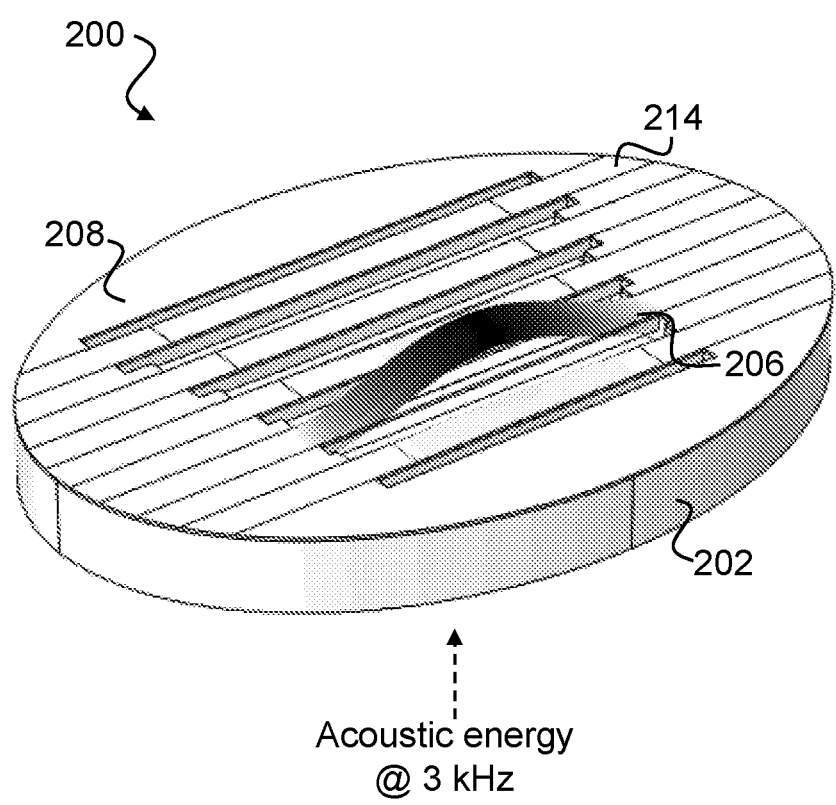
FIG. 3 is a COMSOL model of the device shown in FIGS. 1 and 2 in the presence of a 3 kHz sound pressure wave.

FIG. 3 is a COMSOL model of the acoustic device 200 of FIGS. 1 and 2 showing displacement of one of the beam resonators 206 in response to a sound pressure wave at 3 kHz incident at the external wall 216 of the membrane 202 at Hz. It can be seen that only one of the beam resonators 206 is substantially displaced by sound waves at this frequency. In contrast, the remaining beam resonators 206 are not displaced but remain in their resting position.

It can be seen from FIG. 1 that the beam resonators 206 of the acoustic device 200 vary in length. The piezoelectric beam resonators 206 of the acoustic device 200 may be configured to resonate at specific frequencies or frequency ranges. Thus, each beam resonator 206 is sensitive to incident sound waves having a frequency at or close to its resonant frequency. The array of beam resonators 206 therefore provide passive mechanical frequency selectivity which can be tuned by varying one or more of beam numbers, beam length, beam width, beam thickness, beam composition, beam compliance and other beam characteristics. In the illustrated embodiment, the array may comprise five piezoelectric beam resonators 206 having successively decreasing beam lengths that correspond to five frequency channels (or bands). For application in cochlear implant technology, the above variables may be tuned so that the frequency selectivity of the array of beam resonators 206 at least partially corresponds to cochlear tonotopy. In some embodiments, the array of beam resonators 206 may be a frequency sensitivity which substantially extends across the typical frequency range of human speech, e.g. 100 Hz to 8 kHz.

Figure 4:
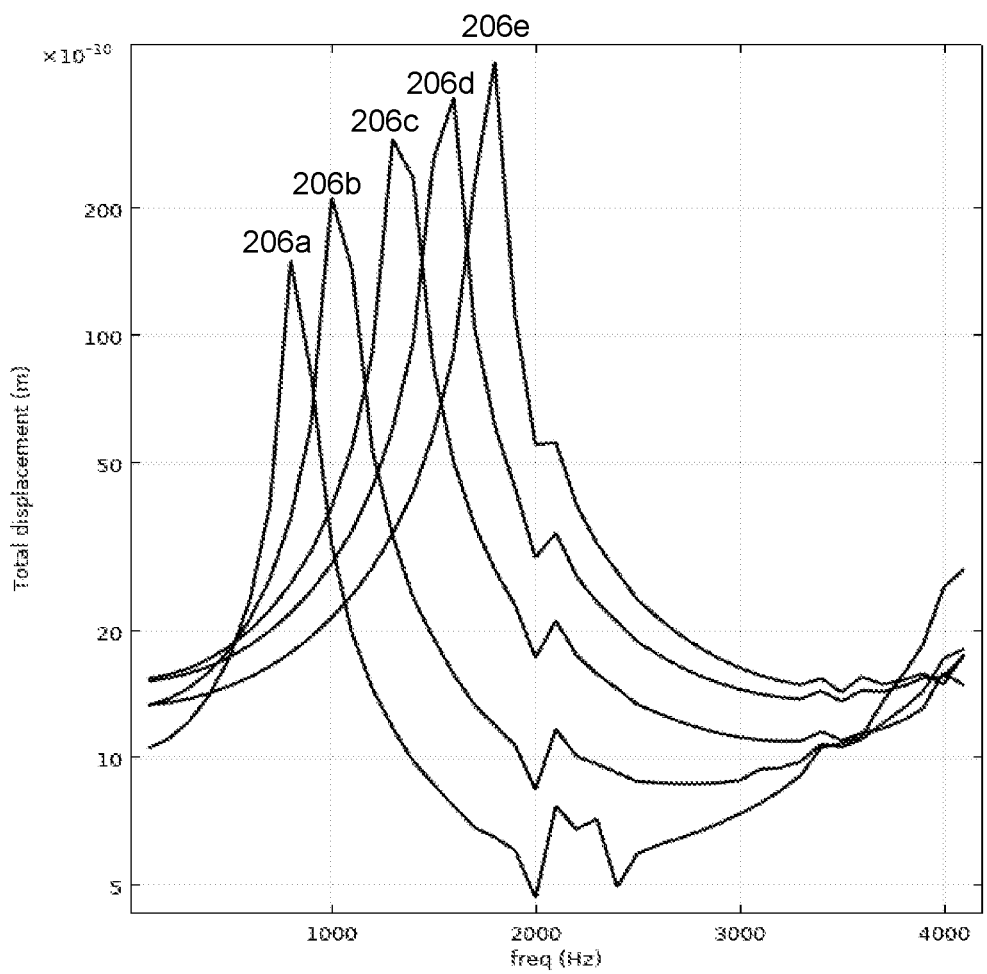
FIG. 4 is a graph of displacement versus frequency for each double-clamped piezoelectric beam resonator of the acoustic device shown in FIGS. 1 and 2, in a first special configuration.

FIG. 4 is a plot showing displacement of five beam resonators 206a:206e, such as the resonators 206 of the acoustic device 200, in accordance with one embodiments, in response to incident sound pressure waves at frequencies between 0 Hz and 4100 Hz. Each beam resonator 206:206e has a different beam length with resonator 206a having the longest beam length and resonator 206e having the shortest beam length. It can be seen that the natural frequency of the resonators 206a:206e increases with decreasing beam length, such that the maximum displacement (and therefore output signal strength) of each of the resonators 206a:206e is at a higher frequency as their beam lengths decrease.

Figure 5:
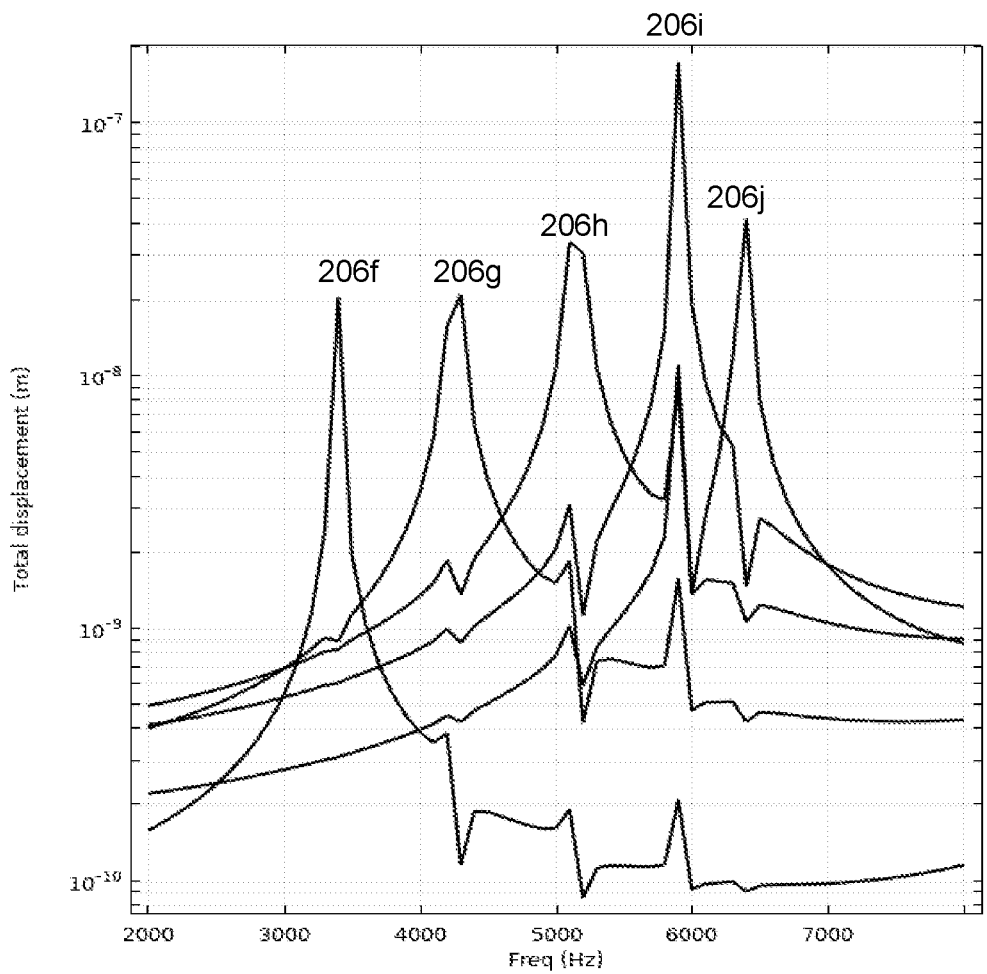
FIG. 5 is a graph of displacement versus frequency for each double-clamped piezoelectric beam resonator of the acoustic device shown in FIGS. 1 and 2, in a second configuration.

FIG. 5 is a plot showing displacement of five beam resonators 206f:206j, such as the beam resonators 206 of the acoustic device 200, in accordance with another embodiment of the disclosure, in response to a tone signal at frequencies between 2000 and 8000 Hz. In this embodiments, the shortest beam resonator 206e relating to FIG. 4 is longer than the longest beam resonator 206f to which FIG. 5 relates. Beam length decreases from resonator 206f to resonator 206j. As with FIG. 4, it can be seen from FIG. 5 that the natural frequency of the resonators 206f:206j increases with decreasing beam length, such that the resonators 206 have a maximum displacement (and therefore output signal strength) at higher frequencies as their beam lengths decrease. However, it can be seen that natural frequency of the longest beam 206f is around 3300 Hz, i.e. greater than the natural frequency of the shortest beam 206e plotted in FIG. 4.

Since the amplitude of the piezoelectrically transduced signals generated at each beam resonator 206 is proportional to the total displacement of the beam resonators 206, it can be seen that by providing an array of beam resonators 206, a plurality of mechanically frequency selective signals can be output from the acoustic device 200. As such, in contrast to conventional microphones which output an electrical signal pertaining to an entire frequency range of human hearing, e.g. 20 to 10000 Hz, the acoustic device 200 may output a plurality of electrical signals relating to frequency sub-bands of the human hearing frequency range. As mentioned above, these frequency ranges can be tuned by adjusting one or more of beam length, beam width, beam thickness, beam composition, and beam compliance, so that they match the tonotopy of the human cochlear.

As mentioned above, adjustment of the number, length and spacing of the plurality of piezoelectric resonators 206 may be used to select a range (or plurality of ranges) of frequencies extracted from sound pressure waves incident at the resonators 206. The number of piezoelectric resonators 206 used in different embodiments may be selectively varied based on the intended use or application of the acoustic device 200. For example, it is believed that a minimum of four channels may be required to deliver enough sound information for human hearing applications of the acoustic device 200, and that 10 channels may be a preferable number based on human cochlear tonotopy. As a result, the number of piezoelectric resonators 206 used when the acoustic device 200 is configured as an in-ear microphone for a cochlear implant or other implantable hearing device may be between 4 and 15, for example, between 6 and 10.

The acoustic device 200 described above may be configured as an acoustic transducer, an acoustic sensor, a microphone, an in-ear microphone for a cochlear implant, and combinations thereof.

Figure 6:
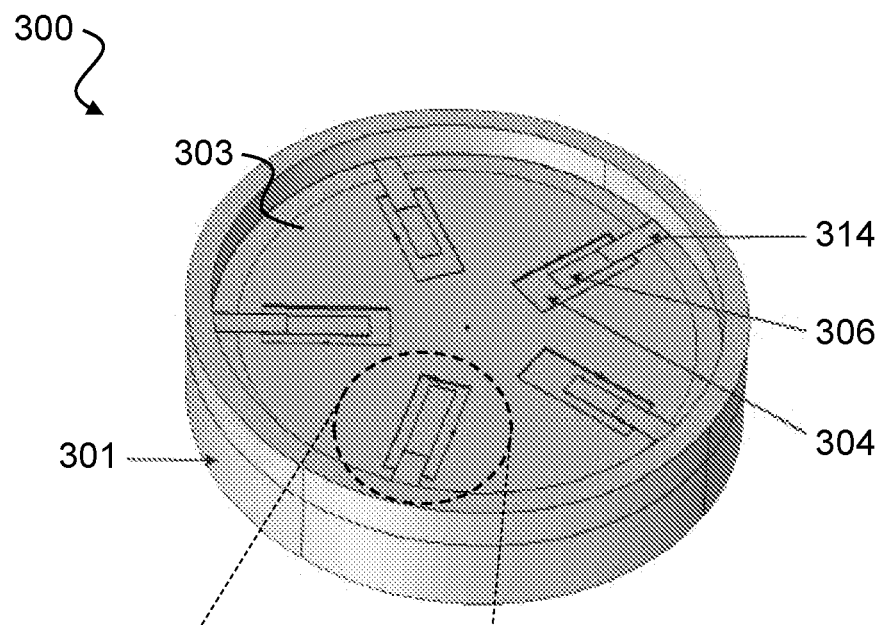
FIG. 6 is a diagram of an acoustic device according to embodiments of the present disclosure.
Figure 7:
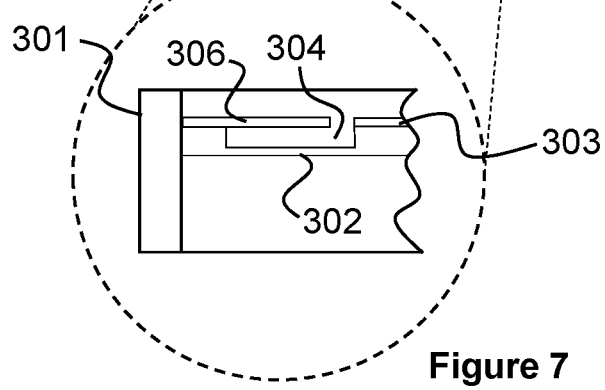
FIG. 7 is a close up view of part of the acoustic device shown in FIG. 6.
Figure 8:
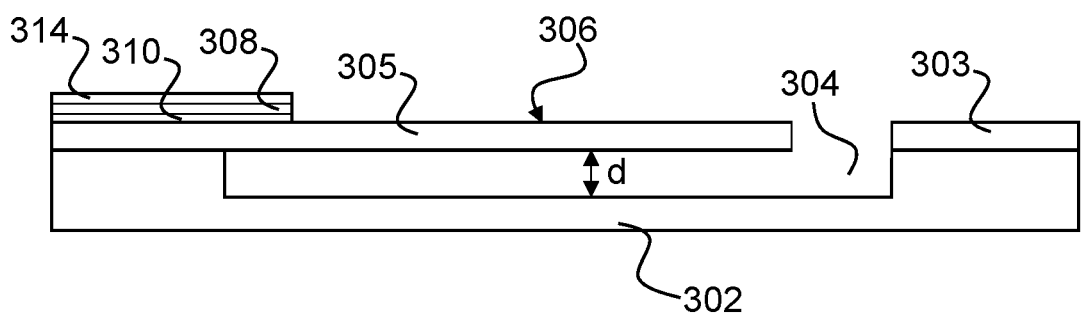
FIG. 8 is a side view of the acoustic device of FIG. 6.

FIGS. 6 to 8 are perspective and side views of an acoustic device 300 according to a further embodiment of the present disclosure. FIG. 7 shows only part of the acoustic device 300 shown in FIG. 6, as denoted by the broken-line circles. FIG. 8 is a more details side view of the part of the acoustic device 300 shown in FIG. 6. The device 300 comprises a support ring 301 which supports an acoustic membrane 302 having a plurality of resonator cavities 304 formed therein, and a piezoelectric resonator 306 supported over each of the cavities 304.

In the embodiment shown, the plurality of resonators 306 are integrally formed as part of a resonator layer 303 disposed over the acoustic membrane 302. By providing the resonator layer 303 over the acoustic membrane 302, low frequency sound path differences around the resonator banks are substantially reduced. As such, the acoustic membrane 302 acts as a baffle increasing the sound shadow at the front and rear surfaces of the device 300. The resonator layer 303 and the acoustic membrane 302 may be glued, laminated or otherwise fixed to one another. The acoustic membrane 302 may have a thickness of between 50 and 150 microns. The resonator layer 303 is preferably thinner than the acoustic membrane 302. In some embodiments, the resonator layer 303 may have a thickness of between 10 and 50 microns, for example 25 microns. In some embodiments, the membrane layer 302 may have a thickness of between 50 and 100 microns, for example 75 microns. The ratio of thicknesses of the acoustic membrane 302 to the resonator layer 303 may be in the region of 2.5-3.5:1. In other embodiments, the acoustic membrane 302 and the resonator layer 303 may be made up of a single layer, the plurality of piezoelectric resonators integrated into the acoustic membrane 302.

The acoustic device 300 may have a total radius of between 500 microns and 20 mm. In some embodiments, the radius of the device may be chosen to conform to a human ear canal. In the embodiment shown, the acoustic device 300 is substantially cylindrical in shape. In other embodiments, the acoustic device 300 may be a different shape, for example, oval, square, or rectangular.

As mentioned above, a piezoelectric cantilever resonator 306 is supported over each of the resonator cavities 304. In some embodiments, each cantilever resonator 306 is fixed to the support ring 301. Additionally or alternatively, each cantilever resonator 306 is fixed to the acoustic membrane 302, for example, using glue or the like. In the embodiment shown, the resonators 306 are coupled to the acoustic membrane 302 through their integration with the resonator layer 303 which in turn is fixed to the acoustic membrane 302. By integrating the resonators 306 into the resonator layer 303, the bulk of the resonator layer 303 (i.e. the portion of the resonator layer 303 other than the resonators 306) acts as a dampener to prevent cross-talk from a resonating one of the resonators 306 to others of the resonators 306. Since the bulk portion of the resonator layer 303 has a much larger mass than each of the resonators 306, its resonant frequency is outside of the range of resonant frequencies of the resonators 306, thus acting to dampen any potential cross-talk between any of the resonators 306.

Each resonator 306 may have a thickness of between 20 and 30 microns, for example, around 25 microns. For example, each resonator 306 may have the same thickness as the remainder of the resonator layer 303 into which it is integrated Minimizing the thickness of the resonator 306 reduces the mass of the resonator 306 and thus the amount of sound pressure required to move the resonator 306. Minimizing the thickness of the resonators 306 may also affect their resonant frequency as has been explained elsewhere in this disclosure.

In some embodiments, the resonator cavity 304 has a depth, d, of between 25 and 100 microns, preferably between 40 and 60 microns, for example around 50 microns. As with the acoustic device 200, the effect of providing a relatively large gap between the acoustic membrane 302 and the cantilever resonators 306 is that it allows for greater displacement of the beam resonators 306. Moreover, the inventors have realised that having a relatively large gap between the resonator 306 and the lower membrane layer 302a, for example greater than 30 microns (preferably around 50 microns) can help mitigate squeeze film damping between layers of the device 300. Excessive squeeze film damping can lead to a breakdown of the band pass frequency response of the resonators 306. The thickness of the membrane 302 below the cavity 304 may be between 20 and 30 microns, for example 25 microns.

Each cantilever beam resonator 306 comprises a free end which is configured to resonate in response to incident sound pressure waves. In the embodiment shown, the cantilever resonators 306 are arranged radially around the acoustic device 300. In other embodiments, the cantilever resonators 306 may be arranged in a non-radial fashion without departing from the scope of the present disclosure. In the embodiments described above, the resonators 306 are cantilever resonators. In other embodiments, the cantilever resonators 306 may be replaced with double clamped beams, for example, as described above with reference to the acoustic device 200. In some embodiments, the cantilever resonators 306 may have a length between 1 and 4 mm.

Each of the piezoelectric cantilever resonators 306 may comprise a cantilever beam 305. To convert the displacement of the cantilever beam 305 into an electrical signal, each piezoelectric cantilever resonator 306 may further comprise a piezoelectric layer 308, a ground layer 310 and an electrode 314. The ground layer 308 may be formed over the cantilever beam 305. The piezoelectric layer 308 may be formed over the ground layer 310. The electrode 314 may be formed over the piezoelectric layer 308. In the embodiment shown, only the cantilever beam 305 is integrated into the resonator layer 303 with the piezoelectric layer 308 and the electrode 314 located on top of the resonator layer 303. In other embodiments one or more of the piezoelectric layer 308, the ground layer 310 and the electrode 314 may be integrated into the resonator layer 303 without departing from the scope of the disclosure.

Each electrodes 314 may be provided over the piezoelectric layer 308 to electrically couple each beam resonator 306 to external sensing electronics (not shown). The piezoelectric layer 308, ground layer 310 and electrodes 314 may be positioned so as not to substantially overlap the resonator cavity 304 or the cantilever resonators 306. Rather, the piezoelectric layer 308, ground layer 310 and electrodes 314 may be positioned at the edges of the device 300 overlapping a portion of the cantilever beam 305. By providing some overlap of the cantilever beam 305 positioned over the acoustic cavity 304, movement of the cantilever beam 305 will cause the piezoelectric layer 308. Increasing the overlap of the piezoelectric layer 308, ground layer 310 and electrodes 314 into the cavity may, however, alter the frequency response of the cantilever beam 305 due to the increased overall mass acting on the cantilever beam 305. In some embodiments only the ground layer 310 and piezoelectric layer 308 extend over the unsupported portion of the cantilever beam 305 over the acoustic cavity 304, with the electrode 304 not extending in such a manner. In some embodiments, the piezoelectric layer 308, ground layer 310 and/or electrodes 314 extend over between 10% and 20% of the length of the cantilever beam 305 located over the cavity 304.

As mentioned above, the electrodes 314 may be coupled to sensing electronics. Sensing electronics may include variable gain amplifiers or operational amplifiers, such as hybrid junction field effect transistor (JFET) operational amplifiers or the like. Sensing circuits may be provided on an application specific integrated circuit (ASIC) or the like which may be coupled to the diaphragm or provided separately. Signal transmission electronics may also be provided with the sensing circuits as will be discussed in more detail below The piezoelectric beam resonators 306, cavity 304, membrane 302 and/or electrodes 314 may be formed by additive manufacturing (or three-dimensional (3D) printing). The additive manufacturing may, for example, comprise projection micro stereolithography (or stereo-lithographic printing (SLP) or digital light processing (DLP)). Suitable projection micro stereolithography techniques and materials are described in 3D *Optical Printing of Piezoelectric Nanoparticle-Polymer Composite Materials*, ACS Nano 8(10), July 2014. In some embodiments, the piezoelectric beam resonators 306, cavity 304, membrane 302 and/or electrodes 314 may be formed by laser cutting sheet (shim) plastic (e.g. polyethylene terephthalate) or metal (e.g. copper or brass) to form one or more layers of the device 300.

The acoustic membrane 302 may be formed from a polymer material, for example, polyethylene glycol diacrylate (PEGDA). The electrodes 314 may be formed from an electrically conductive nanostructure-polymer composite material, for example, a carbon nanotube (CNT)-PEGDA composite material. The piezoelectric layer 308 of the piezoelectric beam resonators 306 may be formed from a piezoelectric nanoparticle-polymer composite material, for example, a barium titanate ($BaTiO_3$, BTO)-PEGDA composite material. Other equivalent conductive and piezoelectric polymer composite materials may also be used. Example materials include $BaTiO_3$, $PbTiO_3$, $Pb(Zr,Ti)O_3$, $Pb(Mg_{1/3}Nb_{2/3})O_3$-$PbTiO_3$, and $(Pb_{0.8725}SM_{0.085})(Ti_{0.98}Mn_{0.02})O_3$.

During operation, sound pressure waves incident the device 300 induce motion in the array of beam resonators 306 which causes changes in capacitive strain in each of the beam resonators 306. In contrast the to the device 200 of FIGS. 1 to 3, sound waves need not be incident at an external wall of the membrane 302. Each beam resonator 306 is configured to resonate at a particular frequency of incident sound pressure waves. When a resonator beam 306 begins to resonate, displacement of the beam 306 towards the acoustic cavity 304 displaces air in the cavity 304 increasing the sound pressure in the cavity 304 below the beam resonator 306. This increase in sound pressure causes the subsequent displacement of the beam resonator 306 away from the acoustic membrane 302 to be substantially larger than it would be in absence of the acoustic membrane 302 (and thus the cavity 304). The inventors have found that the provision of the partially enclosed cavity 304 below the beam resonator 306 can lead to an increase in displacement of a beam resonator 306 of up to 90% or more in some embodiments.

Piezoelectrically transduced signals generated by the piezoelectric layers 308 are then captured by the electrodes 314. The greater the displacement of the resonator beam 305, the greater the voltage produced at the electrode 314.

Figure 9:
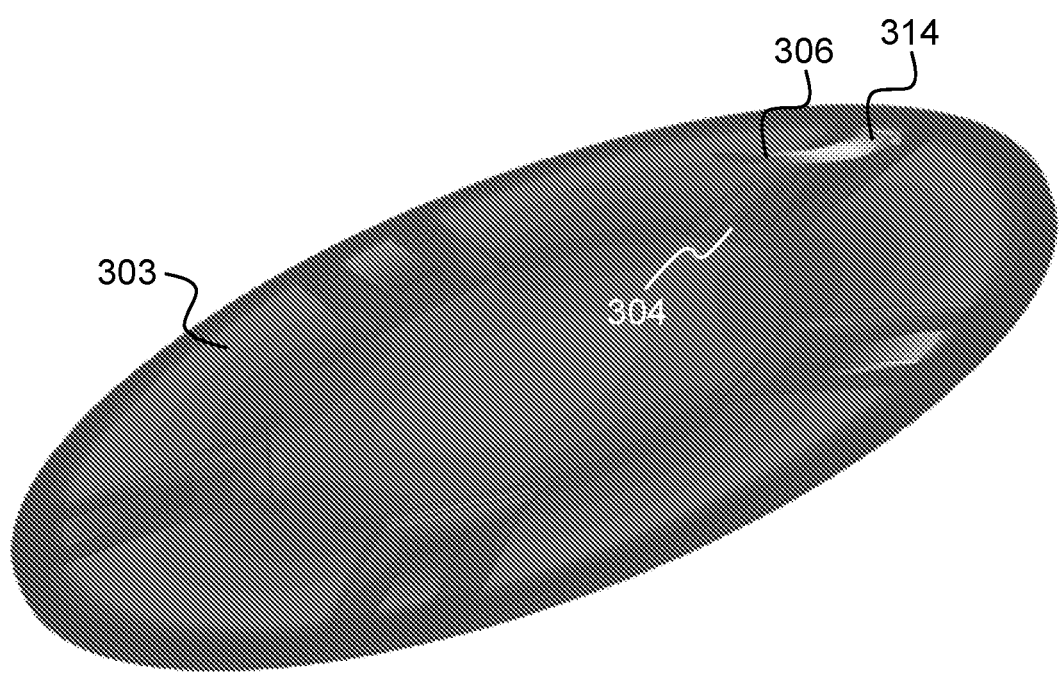
FIG. 9 is a COMSOL model of the device shown in FIGS. 6 to 8 in the presence of a 1800 Hz sound pressure wave.

FIG. 9 is a computer (COMSOL (RTM)) model of the acoustic device 300 of FIGS. 6 to 8 showing displacement of one of the cantilever resonators 306 in response to a sound pressure wave at 1800 Hz incident at the device 300. It can be seen that only one of the cantilever resonators 306 is substantially displaced by sound waves at this frequency. In contrast, the remaining cantilever resonators 306 are not displaced but remain substantially in their resting position.

As with previous embodiments, the cantilever resonators 306 of the acoustic device 300 vary in length. The acoustic device 300 may be configured to resonate at specific frequencies or frequency ranges. Thus, each cantilever resonator 306 is sensitive to incident sound waves having a frequency at of close to its resonant frequency. The array of cantilever resonators 306 therefore provide passive mechanical frequency selectivity which can be tuned by varying one or more of cantilever numbers, cantilever length, cantilever width, cantilever thickness, cantilever composition, cantilever compliance and other cantilever characteristics. Cantilever thickness can be tuned, for example, by changing the thickness of one or more layers of the cantilevers 306. Frequency selectivity may also be tuned, for example, by adjusting the overlap of one or more of the ground layer 310, the piezoelectric layer 308 and the electrode 314, i.e. the extension of such layers over portions of the beam 305 positioned over the cavity 304. In the illustrated embodiment, the five piezoelectric cantilevers 306 are provided having successively decreasing cantilever lengths that correspond to five frequency channels (or bands). The five piezoelectric cantilevers 306 range in length from 2.5 mm to 3.6 mm with resonant frequencies between 3 kHz and 1.3 kHz. However, embodiments of the present disclosure are not limited to such dimensions and resonant frequencies. For application in cochlear implant technology, the above variables may be tuned so that the frequency selectivity of the array of cantilever resonators 306 at least partially corresponds to cochlear tonotopy. In some embodiments, the array of cantilever resonators 306 may have a frequency sensitivity which substantially extends across the typical frequency range of human speech, e.g. 100 Hz to 8 kHz.

Figure 10:
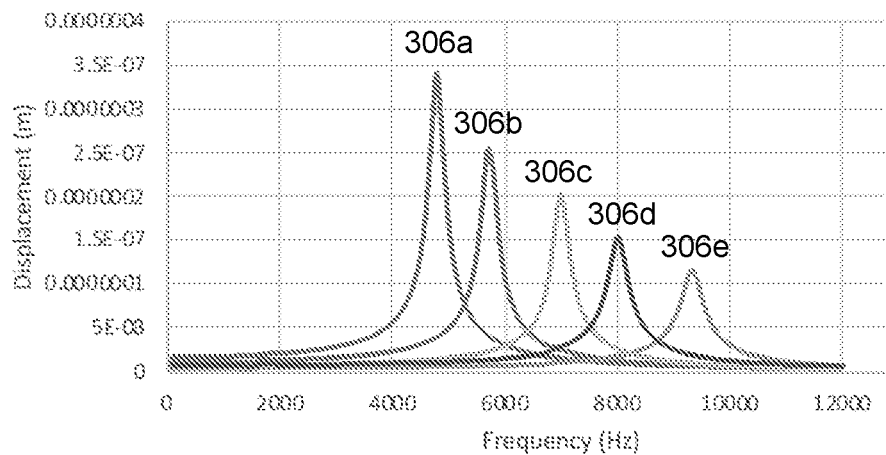
FIG. 10 is a graph of displacement versus frequency for each cantilever piezoelectric beam resonator of one example of the acoustic device shown in FIGS. 6 to 8.

FIG. 10 is a plot showing displacement of five cantilever resonators 306a:306e, such as the resonators 306 of the acoustic device 300, in accordance with some embodiments, in response to incident sound pressure waves at frequencies between 0 Hz and 12000 Hz. The plot in FIG. 10 is based on the COMSOL model of the device 300 shown in FIG. 9.

Figure 11:
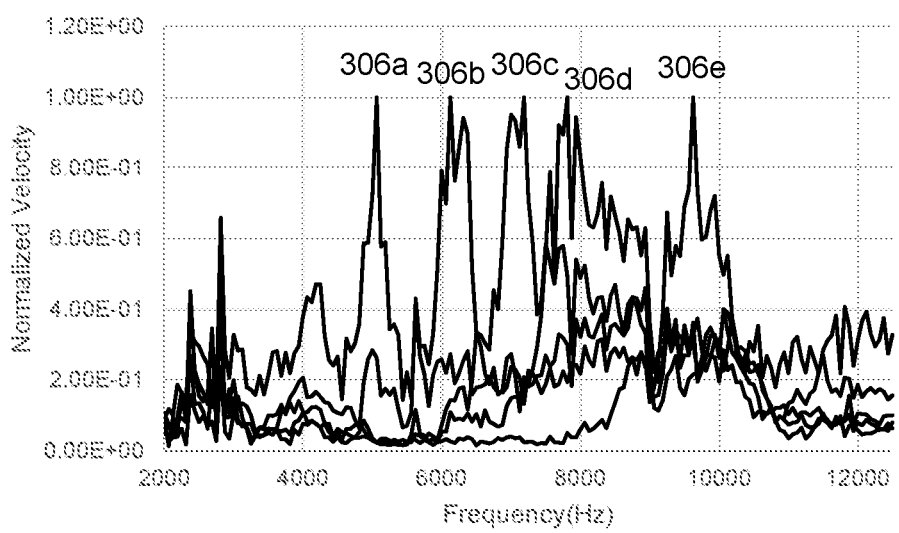
FIG. 11 is a graph of normalised velocity versus frequency for each cantilever piezoelectric beam resonator of one example of the acoustic device shown in FIGS. 6 to 8.

FIG. 11 is a plot showing normalised velocity of five cantilever resonators 306a:306e of an example device physically manufactured based on the model shown in FIG. 9, in response to incident sound pressure waves at frequencies between 0 Hz and 12000 Hz. The five cantilever resonators 306a:306e were thus similar to the resonators 306 of the acoustic device 300. This illustrates the modality of resonance of the five manufactured cantilever resonators 306a:306e, at specific resonant frequencies represented by spikes in the plot extending above the noise floor. In this example, the cantilevers 306a:306e have a resonance at between about 5000 Hz and about 9700 Hz.

Each cantilever resonator 306a:306e has a different cantilever length with resonator 306a having the longest cantilever length and resonator 306e having the shortest cantilever length. It can be seen that the natural frequency of the resonators 306a:306e increases with decreasing cantilever length, such that the maximum displacement (and therefore output signal strength) of each of the resonators 306a:306e is at a higher frequency as their cantilever lengths decrease. This follows for cantilever resonators 306f:306i which are yet longer than the cantilever resonators 306a:306e.

Figure 12A:
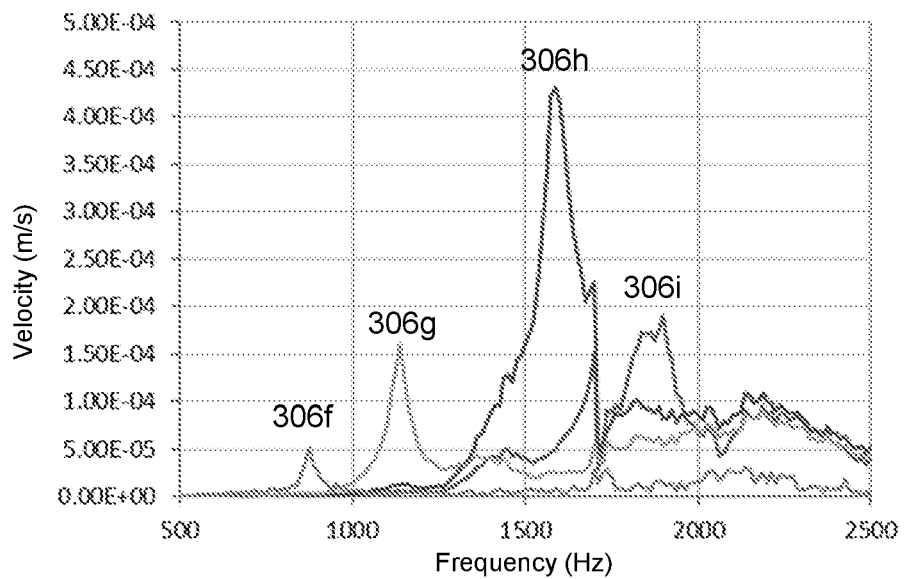
FIG. 12A is a graph of velocity versus frequency for each cantilever piezoelectric beam resonator of one example of the acoustic device shown in FIGS. 6 to 8.
Figure 12B:
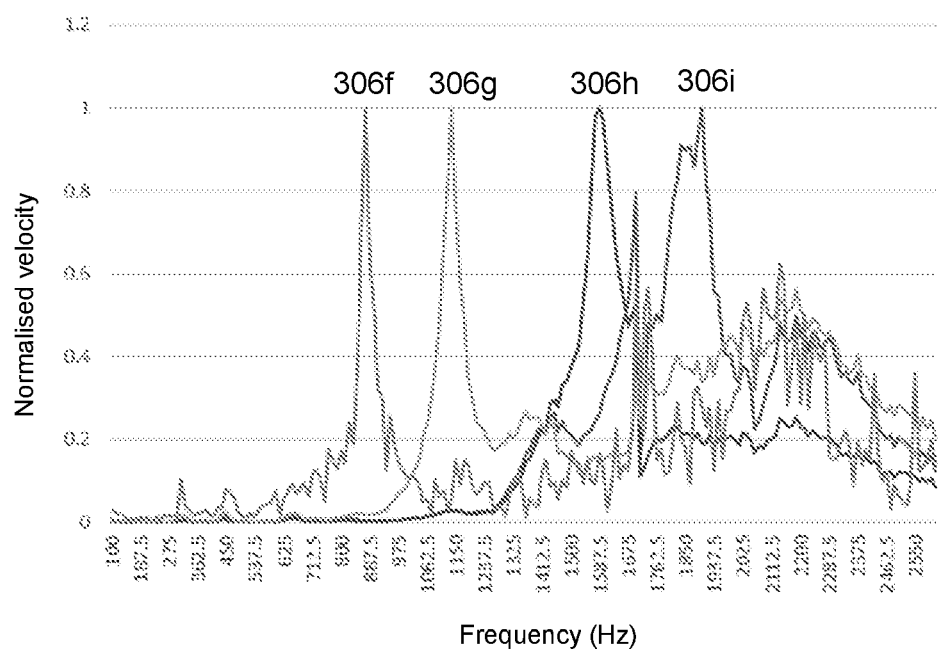
FIG. 12B is a graph of normalised velocity versus frequency for each cantilever piezoelectric beam resonator of one example of the acoustic device shown in FIGS. 6 to 8.

FIG. 12A is another plot showing velocity of a different array of cantilever resonators 306f:306i, such as the resonators of the acoustic device 300 designed to resonate at a lower frequency than those described above with reference to FIGS. 10 and 11 in response to incident sound pressure waves at frequencies between 0 Hz and 4000 Hz. The velocity of displacement of the cantilever resonators 306f:306i was measured using a laser Doppler vibrometer. FIG. 12B is a plot showing normalised velocities of the same four cantilever resonators 306e:306i. FIGS. 12A and 12B further illustrate the modality of resonance of cantilever resonators according to embodiments of the present disclosure, at specific resonant frequencies below 5000 Hz. In this example, the cantilevers 306f:306i have a resonance at between about 800 and 1900 Hz. In this embodiments, the array of cantilever resonators 306f:306i are formed of a plastic (polyethylene terephthalate) having a Young modulus of between $2 \times 10^9$ Pa and $2.5 \times 10^9$ Pa, a Poisson ratio of between 0.3 and 0.35 and a density of between 1000 kg/m$^3$ and 1500 kg/m$^3$.

Figure 13A:
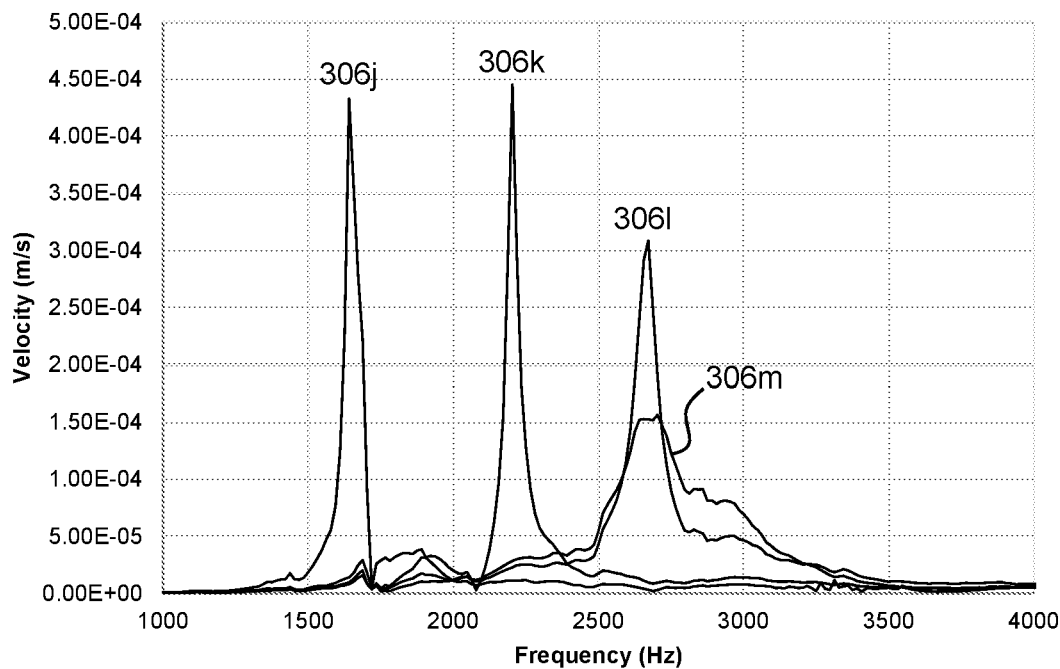
FIGS. 13A and 13B are graphs of velocity versus frequency for each cantilever piezoelectric beam resonator of a pair of examples of the acoustic device shown in FIGS. 6 to 8.
Figure 13B:
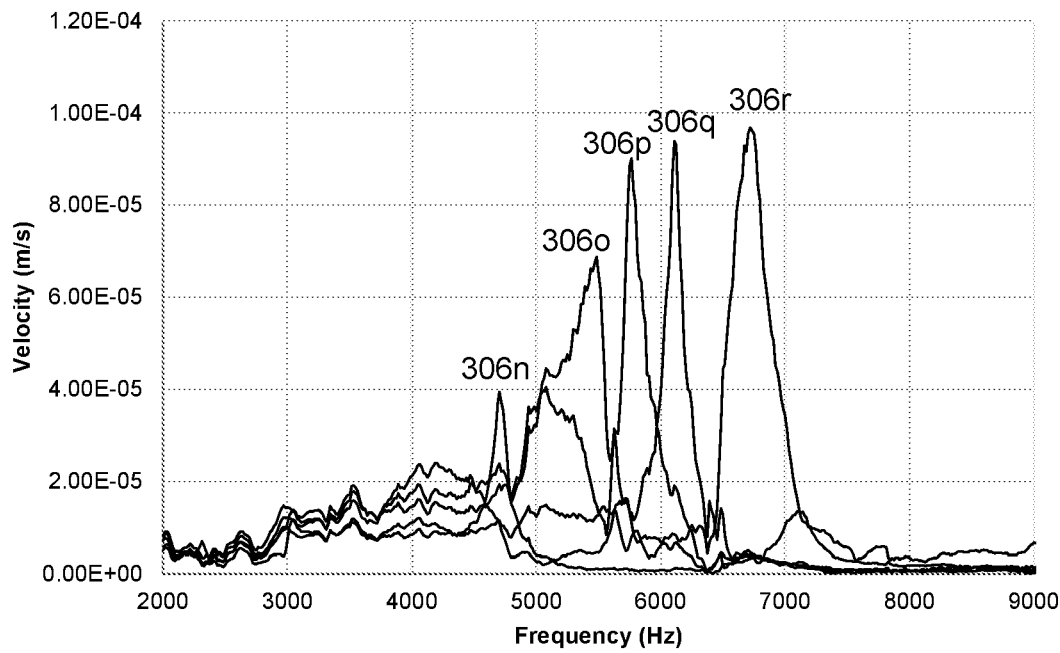

FIGS. 13A and 13B are further plots showing the velocity of displacement of an array of nine cantilever resonators 306k:306r, such as the resonators of the acoustic device 300 designed to resonate through a frequency range from 1500 Hz to 7000 Hz in response to incident sound pressure waves at frequencies spanning the human hearing range. The velocity of displacement of the cantilever resonators 306k:306r was measured using a laser Doppler vibrometer. FIGS. 13A and 13B further illustrate the modality of resonance of cantilever resonators according to embodiments of the present disclosure, at specific resonant frequencies spanning the human hearing range. In this embodiments, the array of cantilever resonators 306k:306r are formed of copper having a Young modulus of between $100 \times 10^9$ Pa and $150 \times 10^9$ Pa (e.g. $110 \times 10^9$ Pa), a Poisson ratio of between 0.3 and 0.35 and a density of between 8000 kg/m$^3$ and 10000 kg/m$^3$ (e.g. 9000 kg/m$^3$).

Figure 14:
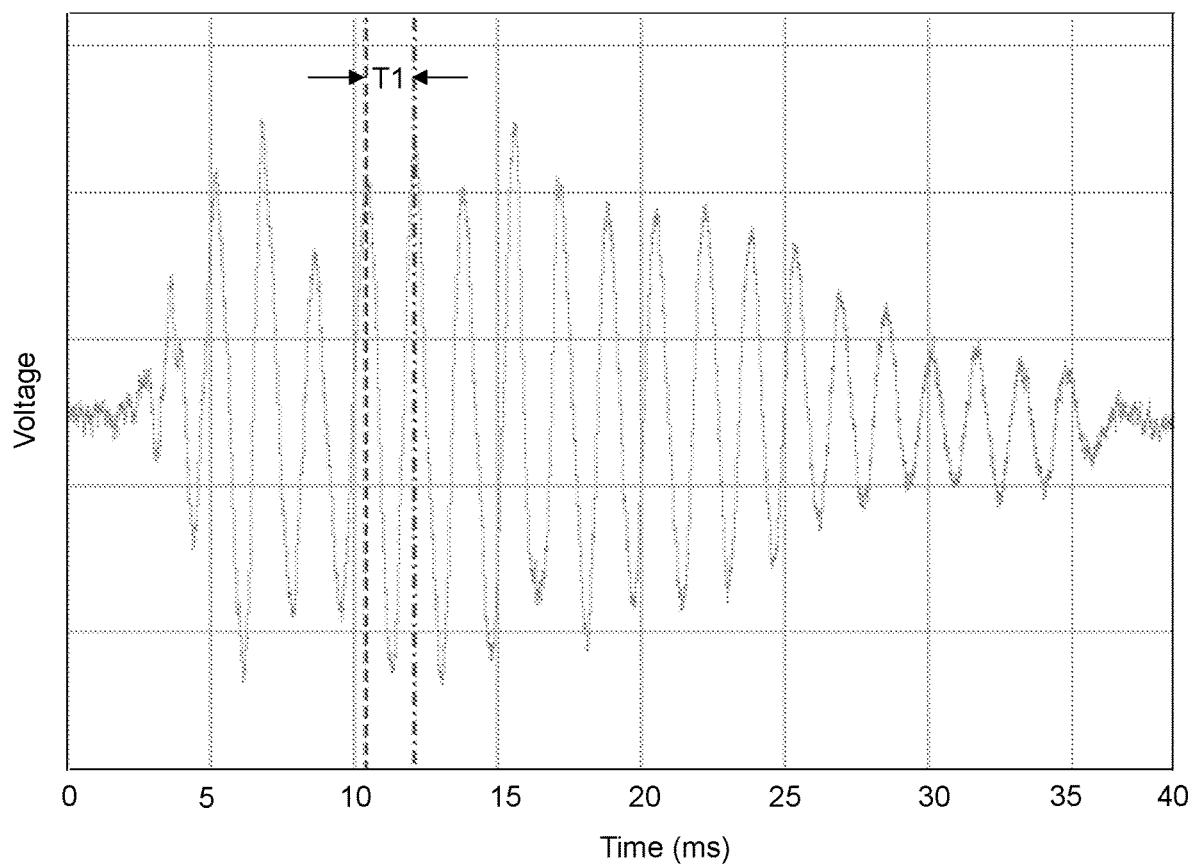
FIG. 14 is a graph of the electrical output from a cantilever piezoelectric beam resonator of one example of the acoustic device shown in FIGS. 6 to 8.

FIG. 14 is a plot showing an example electrical output from a cantilever resonator such as the cantilevers 306 of the acoustic device 300 with a layer polyvinylidene fluoride (PVDF) film forming part of the cantilever resonator. The raw output from the contacted PVDF film was high pass filtered to remove unwanted components below 100 Hz and low pass filtered with a 16 kHz low pass filter to remove noise. The resultant signal is shown in the plot, responsive to narrow band sound incidence at the cantilever resonator, sweeping through a frequency range including the resonant frequency of the cantilever resonator. As the frequency of sound incident at the cantilever resonator moves into the vicinity of the resonant frequency of the cantilever resonator, the cantilever beings to oscillate with greater amplitude and thus the amplitude of the electrical output increases. The time T1 denoted in FIG. 14 is 1.7 ms, giving a resonant frequency of approximately 590 Hz for the subject cantilever.

Figure 15:
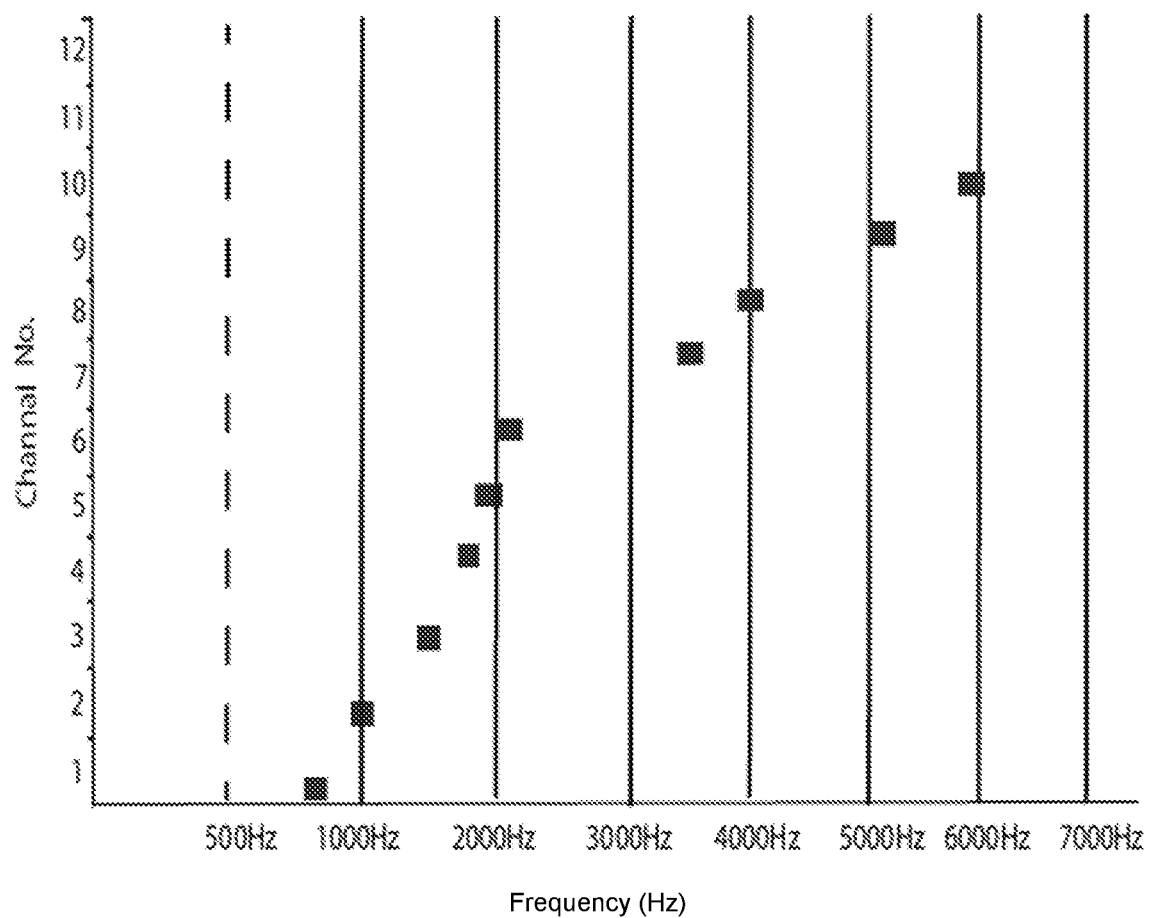
FIG. 15 is a graph showing the resonant frequency of each channel of a pair of acoustic devices such as that shown in FIGS. 6 to 8.

Since the amplitude of the piezoelectrically transduced signals generated at each cantilever resonator 306 is proportional to the total displacement of the cantilever resonators 306, it can be seen that by providing an array of cantilever resonators 306, a plurality of mechanically frequency selective signals can be output from the acoustic device 300. As such, in contrast to conventional microphones which output an electrical signal pertaining to an entire frequency range of human hearing, e.g. 20 to 10000 Hz, the acoustic device 300 may output a plurality of electrical signals relating to frequency sub-bands of the human hearing frequency range. FIG. 15 is a plot showing the resonant frequency of ten cantilever resonators manufactured in accordance with the above, each having a different resonant frequency, the resonant frequencies spanning 800 Hz to 6000 Hz. As mentioned above, frequency ranges can be tuned by adjusting one or more of cantilever length, cantilever width, cantilever thickness, cantilever composition, and cantilever compliance, so that they match the tonotopy of the human cochlear.

The acoustic device 300 described above may be configured as an acoustic transducer, an acoustic sensor, a microphone, an in-ear microphone for a cochlear implant, and combinations thereof.

The acoustic devices 200, 300 described herein may be formed by 3D printing of a plastic material. When configured as an in-ear microphone, one or more components of the acoustic devices described herein may be formed from a soft, bio-compatible, plastic material suitable for being in contact with human skin for extended periods.

Piezoelectric resonators of the various acoustic devices described herein may, for example, be formed from mouldings, laminates and/or films of piezo-polymers, polyvinylidene fluoride (PVDF), and/or piezo-ceramics. Other suitable piezoelectric materials include $BaTiO_3$, $PbTiO_3$, $Pb(Zr,Ti)O_3$, $Pb(Mg_{1/3}Nb_{2/3})O_3$-$PbTiO_3$, and $(Pb_{0.8725}SM_{0.085})(Ti_{0.98}Mn_{0.02})O_3$.

Figure 16:
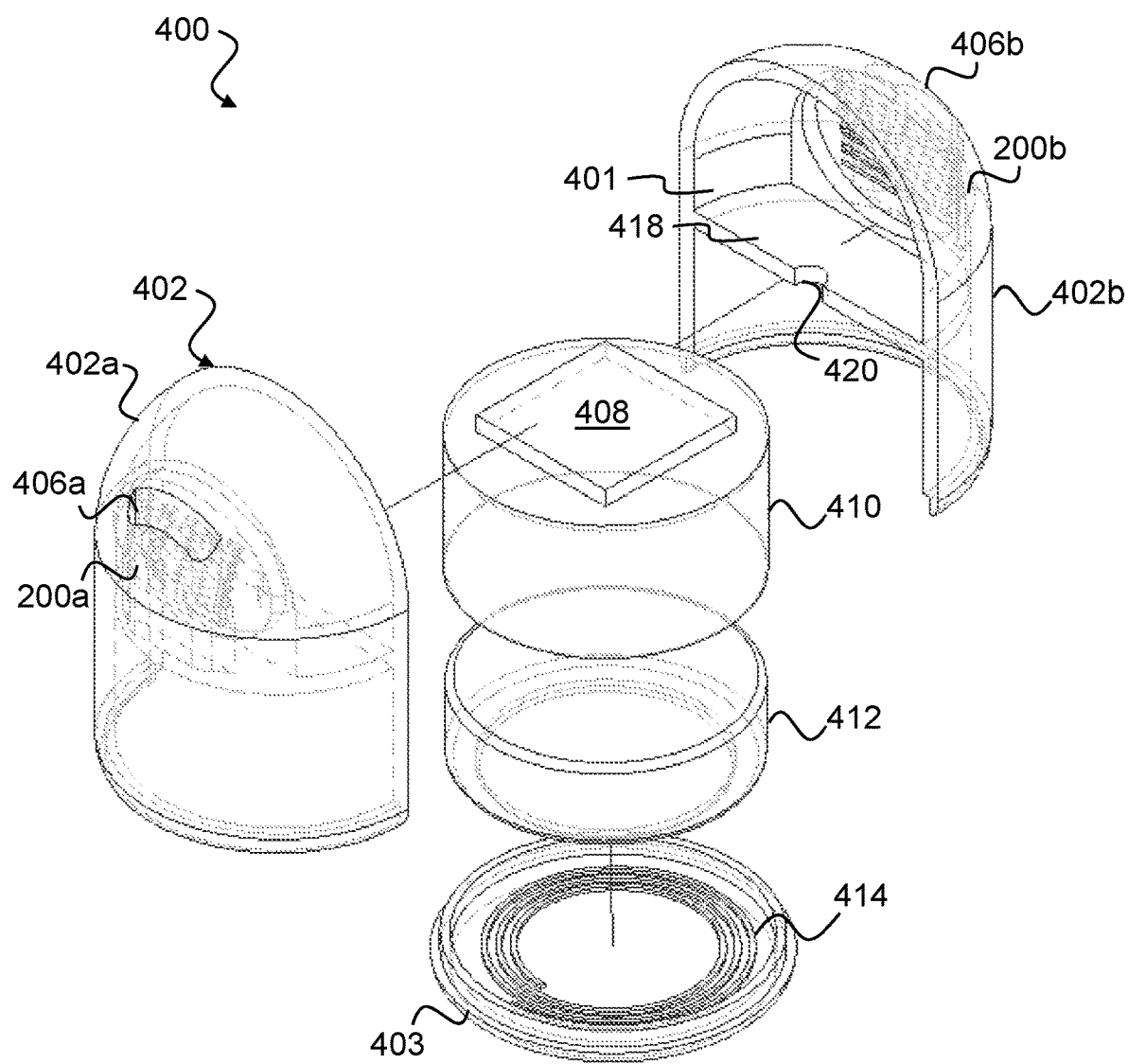
FIG. 16 is an exploded perspective view of an in-ear microphone according to embodiments of the present disclosure.
Figure 17:
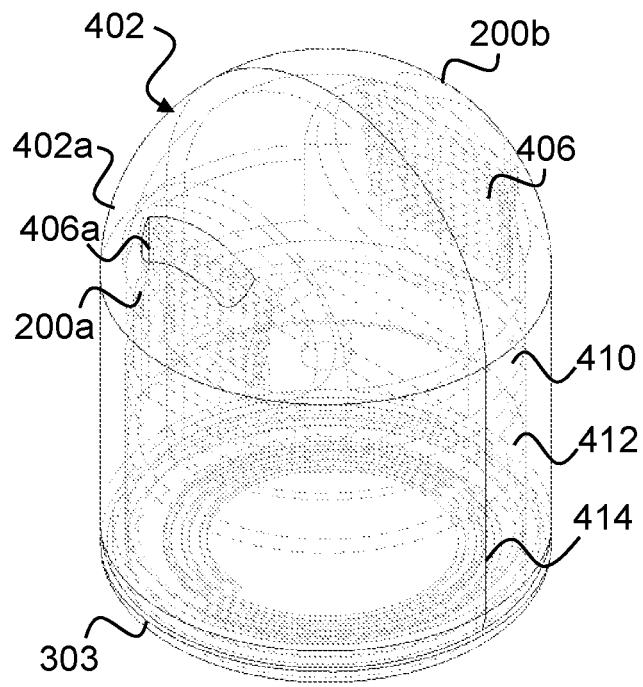
FIG. 17 is a perspective view of the in-ear microphone shown in FIG. 16.
Figures 18, 19:
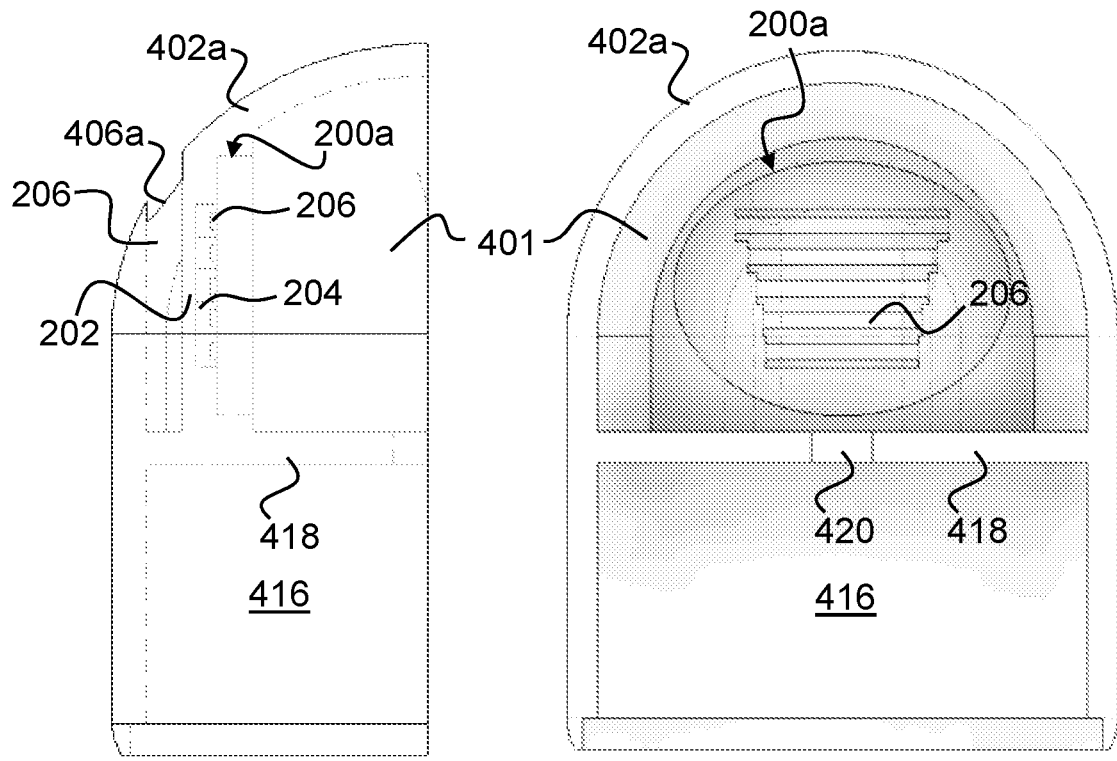
FIG. 18 is a side view of one half of the in-ear microphone shown in FIG. 16.
FIG. 19 is a front cutaway view of one half of the in-ear microphone shown in FIG. 16.

An in-ear microphone 400 according to embodiments of the present disclosure is shown in FIGS. 16 to 19. FIG. 16 shows an exploded view of the in-ear microphone 400. FIG. 17 shows the in-ear microphone 400 in assembled form. FIGS. 18 and 19 show cutaway front and side views respectively of the in-ear microphone 400.

The in-ear microphone 400 comprises an acoustic enclosure 402 shaped and configured to be inserted into an ear canal of a human. Preferably, the acoustic enclosure 402 comprises a cylindrical body shaped to conform to the ear canal. The acoustic enclosure 402 may also comprise a semi-spherical end portion for insertion into an ear canal so as to reduce irritation and risk of injury on insertion.

The acoustic enclosure 402 may be formed of first and second enclosure portions 402a, 402b and an enclosure base 403 as shown in FIG. 16. Alternatively, the first and second enclosure portions 402a, 402b and/or the enclosure base 403 may be manufactured as a single piece. Integrated into each enclosure portion 402a, 402b are acoustic devices 400a, 200b which may be similar to the acoustic device 200 described with reference to FIGS. 1 and 2, or the acoustic device 300 described with reference to FIGS. 6 to 8, the acoustic devices 200a, 200b being separated by a back cavity 301. Each enclosure portion 402a, 402b may be provided with respective acoustic ports 406a, 406b configured to allow the passage of sound pressure waves into the acoustic enclosure 402. The acoustic devices 200a, 200b may be spaced axially apart, their front planar surfaces facing a rotational axis of the acoustic enclosure 402. In some embodiments, the front planar surface of the acoustic devices 200a, 200b are positioned so as to face one another such that the axis of their planar surfaces of each device 200a, 200b substantially parallel to the axis of the cylindrical body of the acoustic enclosure 402. In other embodiments, the acoustic devices 200a, 200b may be distributed longitudinally relative to the rotational axis of the acoustic enclosure 402.

In the embodiments shown in FIGS. 19 to 22 two acoustic device 200a, 200b are provided. It will be appreciated that the present disclosure is not limited to device comprising two acoustic devices. In other embodiments, for example, the in-ear microphone 400 may comprise a single acoustic device, such as the device 200 or device 300 described above, or three or more acoustic devices, such as the device 200 or device 300 described above, positioned within the acoustic enclosure 402. It will also be appreciated that the acoustic devices 200a, 200b may comprise any acoustic device capable of transducing sound waves into electrical signals It will also be appreciated that the acoustic devices 200a, 200b need not be positioned directly opposite each other as shown in FIG. 16. For example, in a variation of the in-ear microphone 400 shown in FIG. 16, the acoustic device 200a, 200b may be spaced along the in-ear microphone 400 in a direction parallel to a longitudinal axis of the microphone 400, provided each acoustic device receives the necessary sound pressure from the acoustic ports 406a, 406b to generate a useful electrical output.

As shown best in FIG. 16, the acoustic enclosure 402 may be configured to enclose one or more of sensing electronics 408 for sensing and processing electrical signals received from the acoustic devices 200a, 200b, a battery housing 410 for housing one or more batteries 412, one or more batteries 412 (if provided), and a transmission coil 414 for wireless transmitting signals processed by the one or more processor 408 to devices external to the in-ear microphone 400. The transmission coil 414 may be positioned next to or integrated into the enclosure base 403 so as to enable the transmission coil 414 to inductively couple to external coils using near field magnetic induction (NFMI) or the like. In some embodiments, external power may be provided to the sensing electronics 408 instead of or in addition to the one or more batteries 412. Such external power may be provided by wire or wirelessly. For example, external power may be wirelessly coupled into the in-ear microphone 400 via one or more coils such as the transmission coil 414. In some embodiments, signals generated by the sensing electronics 408 may be output from the in-ear microphone 400 via wires (not shown). Additionally or alternatively, a wireless transceiver (not shown) may be provided to communicate wirelessly in any manner known in the art with external components, devices or modules. Such a wireless transceiver may, for example, communicate via Wi-Fi (RTM) or Bluetooth (RTM).

The sensing electronics 408, battery housing 410, and transmission coil 414 may be provided in a second cavity 416 which may be separated from the back cavity 401 by a dividing wall 418. An aperture 420 may be provided in the dividing wall 418 to allow electrical connection between each of the first and second acoustic devices 200a, 200b and the sensing electronics 408. The aperture 420 may include a seal (not shown) configured to hermetically seal the aperture 420 whilst allowing electrical connections (such as wires) to pass through the aperture 420.

FIGS. 18 to 19 show the first enclosure portion 402a in more detail. The second enclosure portion 402b is substantially similar to the first enclosure portion 402b except for differences between the acoustic devices 200a, 200b provided therein (as will be described in more detail below). As mentioned above, the acoustic device 200a has a similar construction to the acoustic device 200 described above, and so like parts have been provided like numberings in FIG. 19.

Figure 20:
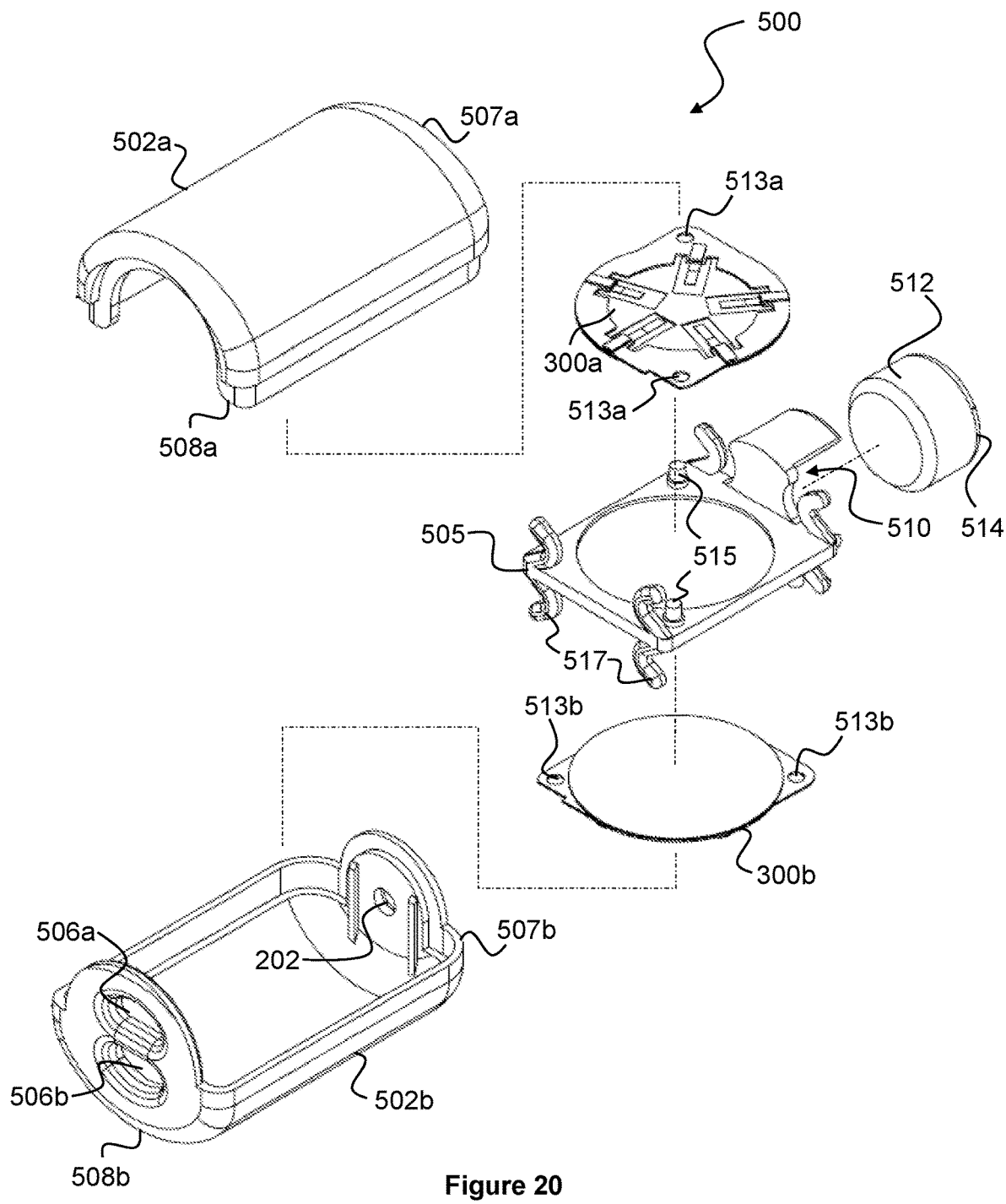
FIG. 20 is an exploded perspective view of an in-ear microphone according to embodiments of the present disclosure.
Figure 21:
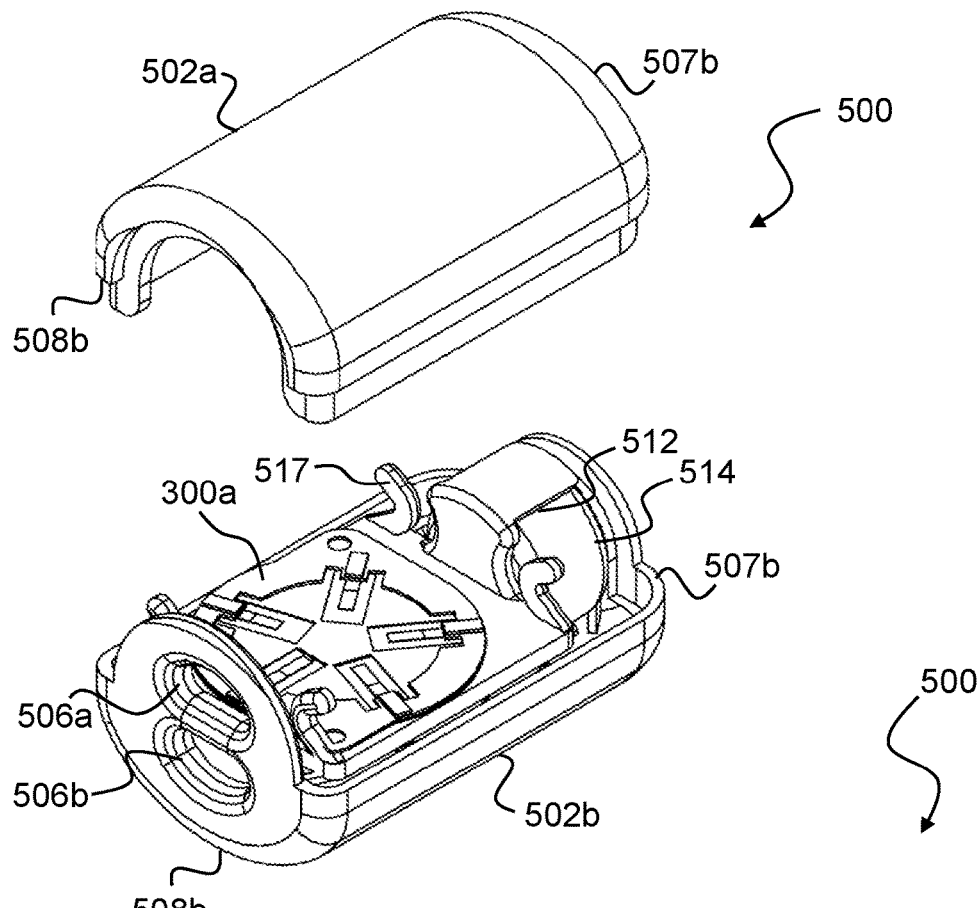
FIG. 21 is a part-exploded perspective view of the in-ear microphone shown in FIG. 20.
Figure 22:
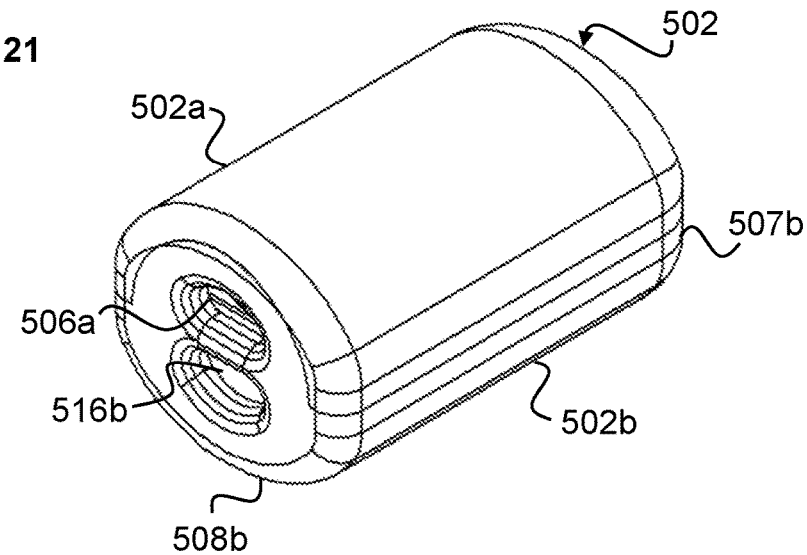
FIG. 22 is a perspective view of the in-ear microphone shown in FIG. 20.

Another in-ear microphone 500 according to embodiments of the present disclosure is shown in FIGS. 20 to 22. FIG. 20 shows an exploded view of the in-ear microphone 500. FIG. 21 shows the in-ear microphone 500 partly assembled with part of the enclosure removed. FIG. 22 shows the in-ear microphone 500 in assembled form.

The in-ear microphone 500 comprises an acoustic enclosure 502 shaped and configured to be inserted into an ear canal of a human. The acoustic enclosure 502 comprises a cylindrical body having a distal end 507 and a proximal end 508, the enclosure 502 shaped to conform to the ear canal. In this embodiments, the acoustic enclosure 502 has an oval cross-section. An oval cross-section may better conform to the human ear canal thereby increasing the overall size of the bud (and thus internal volume for resonators, processing means, and other hardware) without impacting comfort or injury to a user. The enclosure 502 is configured to be inserted, in use, by its distal end 507 into an ear canal. The distal and proximal ends 507, 508 of the enclosure 502 are thus preferably each provided with contoured edges to enable insertion and removal of the microphone 500 into and out of an ear canal without risk of irritation or injury.

The acoustic enclosure 502 may be formed of first and second enclosure portions 502a, 502b configured to enclose all other elements of the microphone 500, as shown in FIGS. 19 and 20. In such embodiments, the first and second enclosure portions 502a, 502b may each comprise coupling elements configured to mutually engage to form the enclosure 502. In other embodiments, the first and second enclosure portions 502a, 502b may be manufactured as a single piece.

The enclosure 502 may be provided with acoustic ports 506a, 506b configured to allow the passage of sound pressure waves into the acoustic enclosure 502 from the proximal end 508 of the enclosure 502 which, when the microphone 500 is inserted into an ear canal, is facing the outside of the ear. In addition, the enclosure 502 may comprise an acoustic port 509 at the distal end 507 of the enclosure 502 configured to allow air to travel through the microphone 500 between the proximal end 508 and the distal end 507. Providing an additional port 509 at the proximal end 508 of the microphone 500 reduces the build-up of pressure within the enclosure 502, thereby improving the flow of sound pressure over the first and second acoustic devices 300a, 300b.

The microphone 500 further comprises a frame 505, for supporting first and second acoustic devices 300a, 300b within the enclosure 502. The first and second acoustic device 300a, 300b may be similar to the acoustic device 300 described with reference to FIGS. 6 to 8 or any other of the acoustic devices described herein. The acoustic devices 300a, 300b may be spaced axially apart, their front planar surfaces facing a rotational axis of the acoustic enclosure 502. In some embodiments, the front planar surface of the acoustic devices 300a, 300b are positioned so as to face one another such that the axis of their planar surfaces of each device 300a, 300b substantially parallel to the axis of the cylindrical body of the acoustic enclosure 502. In other embodiments, the acoustic devices 300a, 300b may be distributed longitudinally relative to the rotational axis of the acoustic enclosure 502. In other embodiments, the acoustic devices 300a, 300b may be angled relative to the rotational axis of the enclosure 502.

The first and second acoustic devices 300a, 300b may be provided with respective mating portions 513a, 513b configured to collocate with mating portions 515 of on the frame 505 so as to secure the position of the first and second acoustic device 300a, 300b relative to the frame 505. The frame 505 may further comprise stabilising members 517 configured to engage with internal walls of the first and second enclosure portions 502a, 502b when the first and second enclosure portions 502a, 502b are brought together in a mating configuration. In doing so, the stabilising members 517 prevent the frame from moving relative to the enclosure portions 502a, 502b when the microphone 500 is fully assembled.

The acoustic enclosure 502 may be configured to enclose one or more of sensing electronics 511 for sensing and processing electrical signals received from the acoustic devices 200a, 200b, a battery housing 510 for housing one or more batteries 512, one or more batteries 512 (if provided), and a transmission coil 514 for wireless transmitting signals processed by the sensing electronics 511 to devices external to the in-ear microphone 500. The transmission coil 514 may be positioned next to or integrated with the one or more batteries 512 proximate the distal end 507 of the enclosure 202 so as to enable the transmission coil 514 to inductively couple to external coils using near field magnetic induction (NFMI) or the like. In some embodiments, external power may be provided to the sensing electronics 508 instead of or in addition to the one or more batteries 512. Such external power may be provided by wire or wirelessly. For example, external power may be wirelessly coupled into the in-ear microphone 500 via one or more coils such as the transmission coil 514. In some embodiments, signals generated by the sensing electronics 508 may be output from the in-ear microphone 500 via wires (not shown). Additionally or alternatively, a wireless transceiver (not shown) may be provided to communicate wirelessly in any manner known in the art with external components, devices or modules. Such a wireless transceiver may, for example, communicate via Wi-Fi (RTM) or Bluetooth (RTM).

The resonators 206, 306 of the acoustic devices 200a, 200b, 300a, 300b may be tuned so as to have a differing natural frequencies and therefore maximum displacements at different frequencies of incident sound pressure waves. For example, the first acoustic device 200a may be configured for low frequency operation and the second acoustic device 200b may be configured for high frequency operation. In some embodiments, the first acoustic device 200a may have a frequency response as shown in FIG. 4 and the second acoustic device 200b may have a frequency response as shown in FIG. 5 such that the combined frequency response of the acoustic device 200a, 200b cover a larger combined frequency range, e.g. 800 Hz to 6500 Hz or the frequency range of human speech. By providing two acoustic devices 200a, 200b spaced axially and opposite one another in the acoustic enclosure 402, a larger frequency range can be covered with more granularity (e.g. 10 channels) whilst maintaining the small form-factor required for the in-ear microphone 400. The above applies similarly to the microphone 500 shown in FIGS. 20 to 22.

The piezoelectric resonators 206, 306, cavity/cavities 204, 304, diaphragm/membrane 202, 302 and electrodes 214, 314 may be formed by additive manufacturing (or three-dimensional (3D) printing). The additive manufacturing may, for example, comprise projection micro stereolithography (or stereo-lithographic printing (SLP) or digital light processing (DLP)). Suitable projection micro stereolithography techniques and materials are described in 3D *Optical Printing of Piezoelectric Nanoparticle-Polymer Composite Materials*, ACS Nano 8(10), July 2014.

Figure 23:
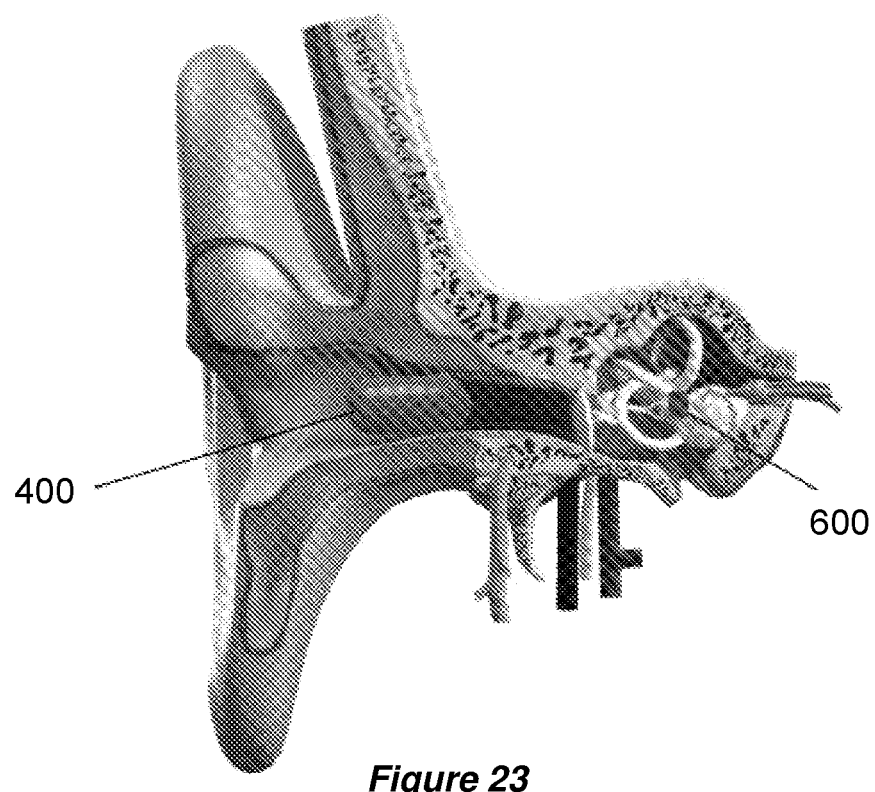
FIG. 23 is an anatomic representation of an in-ear microphone inserted into an ear canal and coupled to a cochlear implant.
Figure 24:
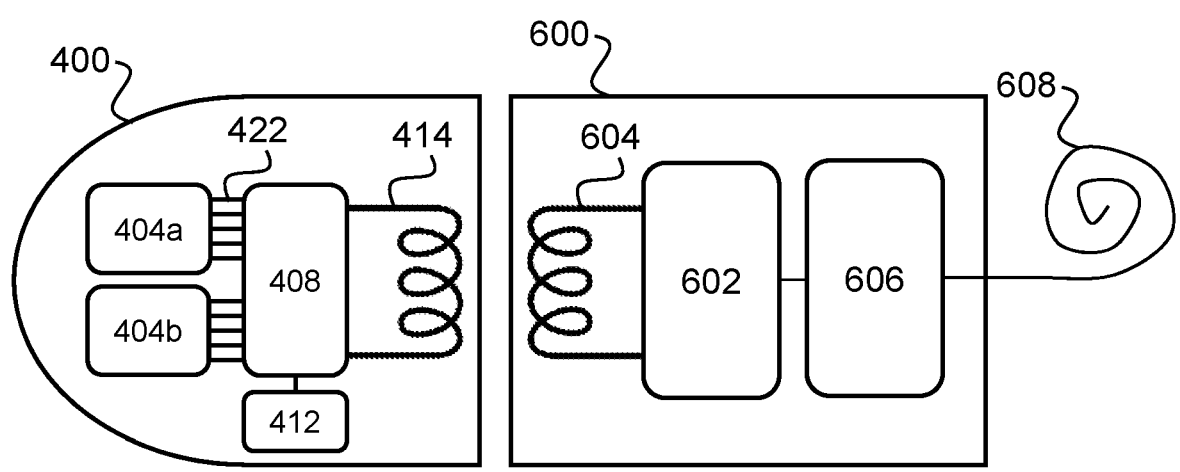
FIG. 24 is a schematic diagram of the in-ear microphone and cochlear implant shown in FIG. 23.
Figure 25:
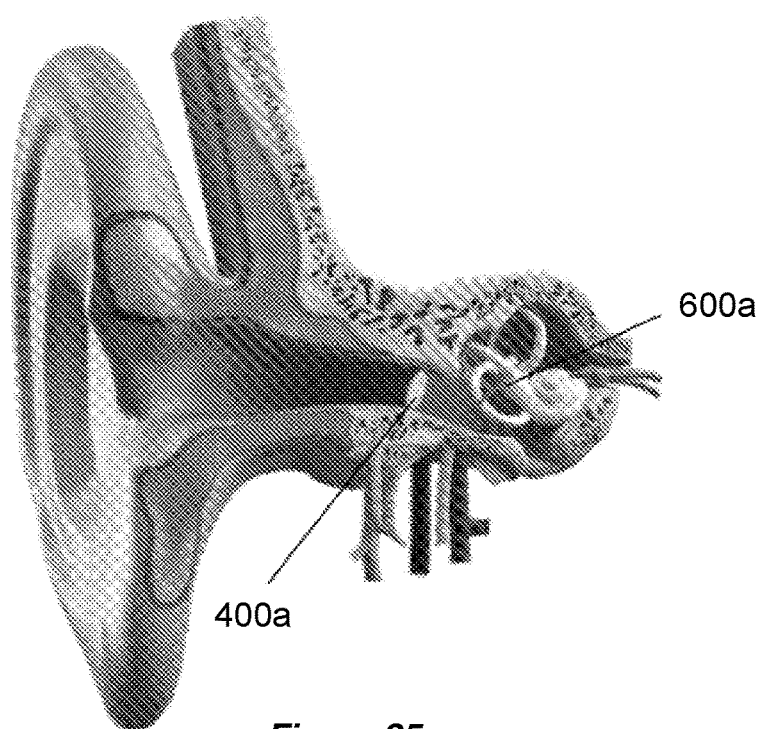
FIG. 25 is an anatomic representation of an in-ear microphone inserted into an ear canal and coupled to a cochlear implant.
Figure 26:
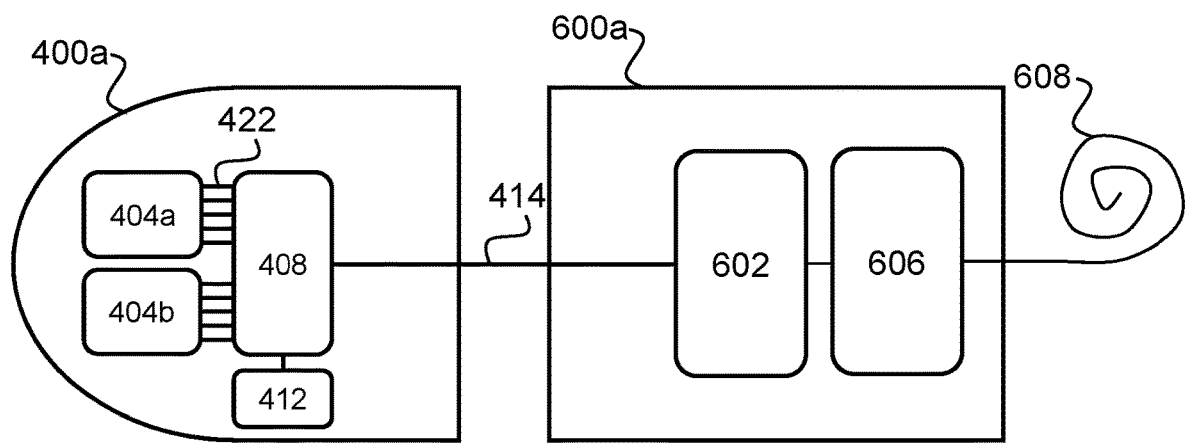
FIG. 26 is a schematic diagram of the in-ear microphone and cochlear implant shown in FIG. 25.

The acoustic devices 200, 300 and/or the in-ear microphones 400, 500 described above may be configured for use with cochlear implants. For example, the in-ear microphones 400, 500 may be configured to transmit, wirelessly or by wire, processed electrical signals relating to beam displacement to a cochlear implant. FIGS. 23 and 24 show the in-ear microphone 400 coupled to a cochlear implant 600 wirelessly. FIGS. 25 and 26 show a variation of the in-ear microphone 400 coupled to a cochlear implant 600a by wire.

FIG. 23 shows the in-ear microphone 400 inserted into an ear canal of a human. FIG. 24 is a schematic diagram of the in-ear microphone 400 and the cochlear implant 600. Electrically active parts of the in-ear microphone 400 including the first and second acoustic devices 200a, 200b, the sensing electronics 408, the transmission coil 414 and battery 412, are illustrated. The cochlear implant 600 comprises a receiver 602 comprising a radio-frequency (RF) coil 604, a processor 606 and an electrode array 608 for stimulating the cochlear nerve (not shown). The receiver 602 is configured for transcutaneous power and data transfer to the processor 606 via the RF coil 602. The processor is configured to process data received by the receiver 602 and stimulate the cochlear nerve accordingly using the electrode array 608. The sensing electronics are configured to transmit via the RF coil 414 stimulation data pertaining to the acoustic devices 200a, 200b to the processor 606 via the receiver 602.

In a variation of the in-ear microphone 400 shown in FIG. 24, instead of or in addition to the transmission coil 414, a wireless transmitter, such as a Wi-Fi (RTM) or Bluetooth (RTM) transmitter may be provided for communicating with and/or providing power to the cochlear implant 600. In which case, the cochlear implant 600 may similarly be provided with a wireless receiver or transceiver (e.g. Bluetooth (RTM) or Wi-Fi (RTM) for receiving and/or transmitting data from/to the in-ear microphone 400 and optionally receiving power from the in-ear microphone 400 or other device.

FIG. 26 shows an in-ear microphone 400a which is a further variation of the in-ear microphone 400 shown in FIG. 23 and a cochlear implant 600a which is a variation of the cochlear implant 600a shown in FIG. 23. Like parts have been given like numbering. In this variation, the in-ear microphone 300a is connected to the cochlear implant 600a by one or more wires 414 over which data and/or power can be delivered to the cochlear implant 600a from the in-ear microphone 400a. In some embodiments, the one or more wires 414 may be interconnected by a percutaneous plug (not shown) of the cochlear implant 600a.

In both embodiments, sensing electronics 408 may be configured to process electrical signals 422 received from the acoustic devices 200a, 200b. Such processing may include filtering, amplification and/or mapping of electrical signals from the piezoelectric resonators 206 of the acoustic devices 200a, 200b to the cochlear implant 600. Advantageously, in contrast to conventional cochlear implant systems which use standard wideband microphones, there is no requirement for the sensing electronics 408 to divide the signal using complex band-pass filtering and post-processing since the signals received from each resonator 206 is already frequency selected.

The above is described in relation to the in-ear microphone 400 of FIGS. 16 to 19, but applies equally to the in-ear microphone 500 of FIGS. 20 to 22.

In the embodiments described above, the in-ear microphones 400, 400a are configured to communicate and/or send or receive electrical power to/from the cochlear implants 600, 600a. However, embodiments of the disclosure are not limited to use with cochlear implants. In other embodiments, the in-ear microphones 400, 400a may be configured to communicate and/or send or receive electrical power to/from any conceivable implantable hearing device, including but not limited to a hearing aid or a bone conduction implant. For example, in-ear microphones described herein may be configured to transmit induced electrical signals to a tympanic-membrane transducer.

Embodiments of the present disclosure provide acoustic devices that are useful as acoustic transducers, acoustic sensors and microphones, including in-ear microphones for cochlear implants. For example, embodiments of the disclosure configured as in-ear microphones for cochlear implants may advantageously improve existing cochlear implant technology by filtering sound mechanically in one step in a small (e.g. 10 mm) space with no time delay and no power input. Embodiments of the in-ear microphones may map sound tonotopically to electrode channels of existing cochlear implants providing discrete frequency selection over multiple channels (over 10 channels). In-ear microphones described herein may sit comfortably within the ear canal to provide 24/7 hearing. Embodiments of the disclosure may take advantage of the pinna's natural contours for direction, amplification and noise cancelling by the brain. Embodiments may be bilaterally implanted due to the absence of time delay meaning that the brain can use both ears. Unwanted body noises may also be filtered due to the high level signal output. Embodiments of the in-ear microphone may replace the external components of existing cochlear implant systems, and provide the discreet factor that users want, removing the visible disability of a cochlear implant, and the lifestyle restrictions of current technology. Embodiments may be easily removed for user self-maintenance, and require fewer implanted components with a consequential reduction in surgery time.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. An acoustic device, comprising:
a device body comprising:
an acoustic membrane having a first surface and a second surface opposite the first surface; and
at least one acoustic cavity formed adjacent the first surface of the acoustic membrane;
a plurality of piezoelectric beam resonators supported over the first surface of the acoustic membrane and separated from the first surface by the at least one acoustic cavity, each of the plurality of piezoelectric beam resonators having at least one different natural frequency;
wherein each of the plurality of piezoelectric beam resonators is configured to oscillate in response to sound pressure waves incident at the piezoelectric beam resonators.

2. The acoustic device of claim 1, wherein each of the plurality of piezoelectric beam resonators differs in one or more of beam length, beam width, beam thickness, beam composition, and beam compliance from the other plurality of piezoelectric beam resonators.

3. The acoustic device of claim 2, wherein the plurality of the piezoelectric beam resonators are planar, parallel to each other, and parallel to the first surface of the acoustic membrane.

4. The acoustic device of claim 1, wherein the at least one acoustic cavity comprises a respective acoustic cavity for each of the plurality of piezoelectric beam resonators.

5. The acoustic device of claim 1, wherein the at least one acoustic cavity comprises a single acoustic cavity for all of the plurality of piezoelectric beam resonators.

6. The acoustic device of claim 1, wherein the plurality of piezoelectric beam resonators comprise four or more piezoelectric beam resonators having successively decreasing beam lengths.

7. The acoustic device of claim 1, wherein the acoustic membrane is circular or oval in shape.

8. The acoustic device of claim 1, wherein the piezoelectric beam resonators are double-clamped piezoelectric beam resonators.

9. The acoustic device of claim 1, wherein the piezoelectric beam resonators are cantilever beam resonators.

10. The acoustic device of claim 1, further comprising a plurality of electrodes on the device body and electrically coupled to the plurality of piezoelectric beam resonators.

11. The acoustic device of claim 10, wherein the electrodes are formed with the piezoelectric beam resonators, acoustic cavity and diaphragm by additive manufacturing or by printed circuit board (PCB) processing.

12. The acoustic device of claim 10, wherein the electrodes are formed from an electrically conductive nanostructure-polymer composite material.

13. The acoustic device of claim 1, wherein the piezoelectric beam resonators are formed from a piezoelectric nanoparticle-polymer composite material.

14. The acoustic device of claim 1, wherein each piezoelectric beam resonator comprises a piezoelectric layer, and wherein each piezoelectric layer extends along a portion of a length of its respective beam resonator adjacent the at least one acoustic cavity.

15. The acoustic device of claim 14, wherein each respective piezoelectric layer extends along between 10% and 20% of the length of its respective beam resonator adjacent the at least one acoustic cavity.

16. The acoustic device of claim 14, wherein each piezoelectric beam resonator further comprises a ground layer in between the piezoelectric layer and the at least one acoustic cavity.

17. The acoustic device of claim 16, wherein each piezoelectric beam resonator further comprises a resonator base on an opposite side of the ground layer from the piezoelectric layer.

18. The acoustic device of claim 1, wherein the acoustic membrane is formed from a polymer material.

19. An in-ear microphone, comprising:
a first acoustic device according to claim 1.

20. The in-ear microphone of claim 19, further comprising:
a second acoustic device according to claim 1, wherein each of the plurality of piezoelectric beam resonators of the first and second acoustic devices have at least one different natural frequency.

21. The in-ear microphone of claim 20, wherein the first and second acoustic devices are configured to transduce acoustic sound pressure waves at low and high frequency bands respectively.

22. The in-ear microphone of claim 19, wherein the in-ear microphone has an oval cross section.

23. The in-ear microphone of claim 20, wherein the first surfaces of each of the first and second acoustic devices are positioned substantially opposite one another, or wherein the second surfaces of each of the first and second acoustic devices are positioned substantially opposite one another.

24. The in-ear microphone of claim 19, further comprising:
an earbud enclosure having a first end, a second end, and the earbud enclosure is adapted for insertion into a human ear canal by the first end.

25. The in-ear microphone of claim 24,
wherein the first acoustic device is located within the earbud enclosure such that the first surface of the first acoustic device faces an axis extending between the first end and the second end of the earbud enclosure, the in-ear microphone further comprising:
a back cavity within the earbud enclosure adjacent the first surface of the first acoustic device, and
a first front cavity within the earbud enclosure adjacent the second surface of the first acoustic device.

26. The in-ear microphone of claim 25, further comprising:
a second acoustic device according to claim 1, wherein each of the plurality of piezoelectric beam resonators of the first and second acoustic devices have at least one different natural frequency, and wherein the second acoustic device is located within the earbud enclosure such that the first surface of the second acoustic device faces the axis extending between the first end and the second end of the earbud enclosure and is adjacent the back cavity, the in-ear microphone further comprising a second front cavity within the earbud enclosure adjacent the second surface of the second acoustic device.

27. The in-ear microphone of claim 26, further comprising a first acoustic port formed in the second end of the in-ear microphone and in communication with the first front cavity and a second acoustic port formed in the second end of the in-ear microphone and in communication with the second front cavity.

28. The in-ear microphone of claim 24, further comprising:
a first front cavity within the earbud enclosure adjacent the first surface of the first acoustic device; and
a first acoustic port formed in the second end of the in-ear microphone and in communication with the first front cavity.

29. The in-ear microphone of claim 28, further comprising:
a rear acoustic port formed towards the first end of the in-ear microphone and in communication with the first front cavity.

30. The in-ear microphone of claim 28, further comprising:
a second front cavity within the earbud enclosure adjacent the first surface of the second acoustic device; and
a second acoustic port formed in the second end of the in-ear microphone and in communication with the second front cavity, wherein the second surfaces of the first and second acoustic devices face an axis extending between the first and second ends of the earbud enclosure.

31. The in-ear microphone of claim 30, further comprising:
a rear acoustic port formed towards the first end of the in-ear microphone and in communication with the first front cavity,
wherein the rear acoustic port is in communication with the second front cavity.

32. The in-ear microphone of claim 24, wherein at least a portion of the earbud enclosure is filled with an acoustic transmission medium.

33. The in-ear microphone of claim 32, wherein the acoustic transmission medium comprises one or more of air, water, or lipids.

34. The in-ear microphone of claim 19, further comprising sensing electronics located within the earbud enclosure and electrically coupled to the plurality of piezoelectric beam resonators, the sensing electronics configured to process electrical signals from each of the plurality of piezoelectric beam resonators.

35. The in-ear microphone of claim 34, wherein the sensing electronics comprises one or more variable gain amplifiers and/or operation amplifiers.

36. The in-ear microphone of claim 35, further comprising a transmitter configured to wired or wirelessly transmit one or more processed signals generated by the sensing electronics.

37. The in-ear microphone of claim 36, wherein the transmitter is a wireless transmitter comprising a inductive coil, located within the earbud enclosure at the first end.

38. The in-ear microphone of claim 36, wherein the transmitter is configured to transmit the one or more processed signals to an implantable hearing device.

39. The in-ear microphone of claim 19 further comprising a power source.

40. The in-ear microphone of claim 19, wherein the earbud enclosure is formed with the first acoustic device by additive manufacturing.

41. The in-ear microphone of claim 19, wherein the earbud enclosure is formed from a biocompatible polymer material.

42. An implantable hearing device, comprising the acoustic device of claim 1.

43. The acoustic device of claim 1, wherein the at least one acoustic cavity has a depth sufficient to allow for displacement of the a plurality of piezoelectric beam resonators in response to the sound pressure waves.

44. The acoustic device of claim 43, wherein the depth is between about 200 and 500 microns.

45. The acoustic device of claim 1, wherein the acoustic membrane includes a first region and a second region, the second region has a thickness thicker than the first region, and the at least one acoustic cavity is formed adjacent the first region.

46. The acoustic device of claim 45, wherein the plurality of piezo electric beam resonators are connected to the acoustic membrane at the second region.

47. The acoustic device of claim 46, wherein the plurality of piezo electric beam resonators are glued to the acoustic membrane.

48. The acoustic device of claim 46, wherein the acoustic membrane further includes a third region, the third region has a thickness thicker than the first region, and the plurality of piezo electric beam resonators are connected to the acoustic membrane at the third region.

* * * * *